US006111079A

United States Patent [19]
Wylie et al.

[11] Patent Number: 6,111,079
[45] Date of Patent: Aug. 29, 2000

[54] LEAD BINDING POLYPEPTIDES AND NUCLEOTIDES CODING THEREFORE

[75] Inventors: Dwane E. Wylie; Osvaldo Lopez, both of Lincoln; Peter Joseph Murray, Omaha; Peter Goebel, Lincoln, all of Nebr.

[73] Assignee: Bionebraska, Inc., Lincoln, Nebr.

[21] Appl. No.: 08/767,128

[22] Filed: Dec. 4, 1996

Related U.S. Application Data

[63] Continuation-in-part of application No. PCT/US96/09258, Jun. 5, 1996, which is a continuation-in-part of application No. 08/541,373, Oct. 10, 1995, abandoned, which is a continuation-in-part of application No. 08/462,798, Jun. 5, 1995, abandoned.

[51] Int. Cl.$^7$ .......................... C12P 21/08; C07K 16/44; C07H 21/04; C07H 21/02
[52] U.S. Cl. .................... 530/387.3; 530/387.1; 530/388.1; 530/388.9; 530/395; 536/23.1; 536/23.4; 536/23.5; 536/23.53
[58] Field of Search .................... 530/387.1, 388.9, 530/395, 387.3, 388.1; 536/23.53, 23.1, 23.4, 23.5

[56] References Cited

U.S. PATENT DOCUMENTS

| | | |
|---|---|---|
| 4,078,049 | 3/1978 | Felix et al. . |
| 4,281,065 | 7/1981 | Lin et al. . |
| 4,454,106 | 6/1984 | Gansow et al. . |
| 4,456,691 | 6/1984 | Stark . |
| 4,472,509 | 9/1984 | Gansow et al. . |
| 4,474,893 | 10/1984 | Reading . |
| 4,530,786 | 7/1985 | Dunbar et al. . |
| 4,608,337 | 8/1986 | Croce . |
| 4,668,771 | 5/1987 | Kawakami et al. . |
| 4,677,070 | 6/1987 | Larrick et al. . |
| 4,681,782 | 7/1987 | Ozkan . |
| 4,701,408 | 10/1987 | Koestler . |
| 4,722,892 | 2/1988 | Meares et al. . |
| 4,731,238 | 3/1988 | Neville et al. . |
| 4,760,155 | 7/1988 | Heffernan et al. . |
| 4,760,156 | 7/1988 | Heffernan et al. . |
| 4,762,781 | 8/1988 | Geffard . |
| 4,764,359 | 8/1988 | Lemelson . |
| 4,772,551 | 9/1988 | Hart et al. . |
| 4,778,752 | 10/1988 | Curtiss et al. . |
| 4,793,986 | 12/1988 | Serino et al. . |
| 4,797,473 | 1/1989 | Tarsio et al. . |
| 4,859,613 | 8/1989 | Lawrence . |
| 5,055,562 | 10/1991 | Koganty . |
| 5,112,606 | 5/1992 | Shiosaka et al. . |
| 5,112,738 | 5/1992 | Buckler et al. . |
| 5,354,652 | 10/1994 | Silbergeld . |
| 5,464,759 | 11/1995 | Coolidge et al. . |
| 5,532,136 | 7/1996 | Carlson . |
| 5,595,887 | 1/1997 | Coolidge et al. . |
| 5,620,856 | 4/1997 | Carlson . |

FOREIGN PATENT DOCUMENTS

| | | |
|---|---|---|
| 173 629 | 4/1986 | European Pat. Off. . |
| 235 457 | 9/1987 | European Pat. Off. . |
| 286 323 | 10/1988 | European Pat. Off. . |
| 2 527 928 | 9/1983 | France . |
| WO 86/01407 | 3/1986 | WIPO . |
| 90/10709 | 9/1990 | WIPO . |
| WO 91/16912 | 11/1991 | WIPO . |
| WO 92/01781 | 2/1992 | WIPO . |
| WO 92/01939 | 2/1992 | WIPO . |
| 9418220 | 8/1994 | WIPO . |
| WO 95/18156 | 7/1995 | WIPO . |

OTHER PUBLICATIONS

Advertisement for BiMelyze® Mercury Assay Kit published in Mar./Apr. 1991 issue of Journal of Analytical Toxicology (vol. 15).
Advertisement for BiMelyze® Mercury Assay Kit published in the Sep. 1991 issue of Journal of the American Water Works Association (vol. 15).
Aviv et al., *Proc. Natl. Acad. Sci. USA,* 69, 1408 (1972).
Baker et al., *J. Biol. Chem.,* 253, 8444–8451 (1978).
Jang et al., *Heavy Chain Dominance in the Binding of Native DNA by a Lupus Mouse Monoclonal Antibody,* Medline, MM23047, Apr. 16, 1995.
Barbas et al., *Proc. Natl. Acad. Sci. USA,* 88, 7978 (1991).
BiMelyze® Mercury Assay Kit sales brochure available to the public in Dec. 1990.
BiMelyze® Mercury Assay Protocol.
Baum et al., *Chem. and Eng. News,* 19–20 (Jan. 23, 1989).
Bizollon et al., *Monoclonal Antibodies and New Trends in Immunoassays,* Ch. A, 53–58 (1984).
Butler et al., *Advances in Immunol.,* 17, 255–310 (1973).
Caise, *Methods in Enzymology,* 92, (Academic Press, 1983) at 445–458.
Cenini, *Comp. BioChem. Physiol.,* 81C, 213–217 (1985).
Clarke et al., *J. Immunol. Methods,* 137, 65–72– (1991).
Cress et al., *ABL,* 16–19 (Feb., 1989).
Cwirla et al., *Proc. Natl. Acad. Sci. USA,* 87, 6378–6382 (1990).
"EPA Industrial Toxics Project", BioNebraska, Inc. (Jan. 1991).
Erlanger, *Methods of Enzymology,* 70, 85–104 (1980).
Evans et al., *BioTechniques,* 8, 357 (1990).
Forghieri et al., *Aust. J. Chem.,* 36, 1125–1132 (1983).
Friguet et al., *J. Immunol. Methods,* 77, 305–319 (1985).
Fuhr et al., *J. Am. Chem. Soc.,* 85, 6944 (1973).
Gigliotti et al., *J. Infect. Dis.,* 149, 43–47 (1982).
Gillespie et al., *Chemistry,* Allyn and Bacon Inc., 767–769 (1986).
Hainfeld, *Nature,* 333, 281–282 (1988).

(List continued on next page.)

*Primary Examiner*—Paula K. Hutzell
*Assistant Examiner*—Geetha P. Bansal
*Attorney, Agent, or Firm*—Merchant, Gould, Smith, Edell, Welter & Schmidt, P.A.

[57] ABSTRACT

Metal binding polypeptides which include an amino acid sequence coding for a light chain variable region of a monoclonal antibody capable of immunoreacting with a lead cation and nucleotides which include a nucleic acid sequence coding for the variable region are provided. The invention is also directed to fusion proteins and Fab fragments which include the light chain variable region.

19 Claims, 13 Drawing Sheets

OTHER PUBLICATIONS

Hawley's *Condensed Chemical Dictionary*, p. 748 (11th Edition).
Hohlfeld et al., *Monogr. Allergy*, 25, 50 (1988).
Horton et al., *Gene*, 77, 61–68 (1989).
Huse et al., *Science*, 246, 1275–1281 (19890.
*Immunology: The Science of Self–Nonself Discrimination*, Jan Klein, editor, John Wiley & Sons, NY publisher; at p. 348 (1972).
Iverson et al., *Science*, 243, 1184–1188 (1989).
Kabakoff, *Enzyme Immunoassay*, Meggio, CT, ed., CVC Press, FL, 78–88 (1980).
Karin, *Cell*, 41, 9–10 (1985).
Kenmotsu, *Chem. Abstracts*, 13, 107669m (1984).
Kohler et al., *Nature*, 256, 495 (1975).
Kudsk, *Chem. Abstracts*, 82, 11898t (1973).
Langan et al., *J.A.D.A.*, 115, 867–880 (1987).
Lerner et al., *T.I.B.S.*, 12, (no page nos.) (1987).
Lerner et al., *Sci. Amer.*, 258, 58–70 (1988).
Lewis et al., *J. Lab. Clin. Med.*, 88, 375–388 (1976).
Lindgarde et al., *Scand. J. Immunol.*, 3, 277–285 (1974).
Magos et al., *Chem. Abstracts*, 90, 98118a (1978).
Massey, *Nature*, 328, 457–458 (1987).
Matsui et al., *J. Biol. Chem.*, 260, 4174–4179 (1985).
Meares, "Attaching Metal Ions to Antibodies," 190th ACS National Meeting, Department of Chemistry, University of CA, Abstract (Sep., 1985).
Meares, *Nucl. Med. Biol.*, 13, 311–318 (1986).
Merlini et al., *Clin. Exp. Immunol.*, 69, 148–156 (1987).
Mesna et al., *Comp. Biochem. Physiol.*, 99B, 181–185 (1991).
Naito, *Chem. Abstracts*, 95, 92911k (1980).
Napper et al., *Science*, 237, 1041–1043 (1987).
Ohara et al., *Nature*, 315, 333–336 (1985).
Parmley et al., *Gene*, 73, 305–318 (1988).
Patterson et al., *Am. Rev. Resp. Dis.*, 120, 1259–1267 (1979).
Pierce, *J. Occup. Med.*, 28, 589–592 (1986).
Pinekard, *Handbook in Exp. Immunology*, 3rd ed., Blackwell Scientific, publishers, 17.7–17.23 (1978).
Pollack et al., *Science*, 234, 1570–1573 (1986).
Reardan, *Dialog Information Services*, File 35: Dissertation Abstracts Online 1861 Jun. 90, Dialog Accession No. 894111, vol. 46/07–B of Dissertation Abstracts International, p. 2326, (1985).
Reardan et al., *Nature*, 316, 265–268 (1985).
Roitt et al., *Immunology*, p. 5.8 (1989).
Rubinstein et al., *Nature*, 332, 426–429 (1988).
Sanger et al., *Proc. Natl. Acad. Sci. USA*, 74, 5463 (1977).
Sarkar et al., *Biotechniques*, 8, 404–407 (1990).
Sastry et al., *Proc. Natl. Acad. Sci. USA*, 86, 5728 (1989).
Schuster et al., *Biologie Prospective, C.R. Colloq. 8th*, 371–376 (1993).
Shirakawa et al., *Clinical Allergy*, 18, 451–460 (1988).
Shirakawa et al., *Chest*, 95, 29–37 (1989).
Shirakawa et al., *Clin. Exp. Allergy*, 22, 213–218 (1992).
Short et al., *Nucleic Acids Res.*, 16, 7583–7600 (1988).
Spitalny et al., *J. Exp. Med.*, 159, 1560–1565 (1984).
Stinson, *Chem. Eng. News*, 30–33 (Oct. 19, 1987).
Torchilin et al., *Hybridoma*, 6, 229–240 (1987).
Tramontano et al., *Science*, 234, 1566–1569 (1986).
Treagan, *Biol. Trace Element Res.*, 1, 141–148 (1979).
Van Regenmortel, *T.I.B.S.*, 11, 36–39 (1986).
Verhoeyen et al., *Science*, 239, 1534–1536 (1988).
Wade et al., *J. Am. Chem Soc.*, 115, 4449–4456 (1993).
Waters et al., *DOE Methods for Evaluating Environmental and Waste Mangement Samples*, (1993).
Waters et al., *Govt. Reports Accouncements & Index*, Issue 24 (1993).
Wide et al., *BioChem. BioPhys. Acta.*, 130, 257–260 (1966).
Williams, *Nature*, 332, 393 (1988).
Wylie et al., *Anal. Biochem.*, 194, 381–387 (1991).
Wylie et al., *PNAS–USA*, 89, 4104–4108 (May, 1992).
Yamamoto et al., *J. Immunol. Methods*, 22, 309–317 (1978).
Yanisch–Perron et al., *Gene*, 33, 103–119 (1985).
Yelton et al., *Hybridoma*, 1, 5–11 (1981).
Kubota et al., *Immunology Letter*, 14:53–58, (1986–87).
Dzierdak et al., *J. Immunology*, 136:1964–1870 (1986).
Barbas III, et al. 1993. PNAS, 90:6385–6389, 1993.
Hoogenboom, HR. et al. 1991. Nucleic Acid Res, 19:4133–4137, 1991.

FIG. 1A

Sequences of Heavy Chains of Lead-Specific Antibodies

Sequences of Heavy Chains of Lead-Specific Antibodies

```
                                              110
6B11    Trp Gly Gln Gly Thr Leu Val Thr Val Ser Ala
        TGG GGC CAA GGG ACT CTG GTC ACT GTC TCT GCA

1254    Trp Gly Gln Gly Thr Leu Val Thr Val Ser Ala
        TGG GGC CAA GGG ACT CTG GTC ACT GTC TCT GCA

8E7     Trp Gly Gln Gly Thr Ser Val Thr Val Ser Ser
        TGG GGT CAA GGA ACC TCA GTC ACC GTC TCC TCA

10G5    Trp Gly Gln Gly Thr Leu Val Thr Val Ser Ala
        TGG GGC CAA GGG ACT CTG GTC ACT GTC TCT GCA

14F21   Trp Gly Ala Gly Thr Thr Val Thr Val Ser Ser
        TGG GGC GCA GGG ACC ACG GTC ACC GTC TCC TCA
```

FIG. 1B

Sequences of Light Chain Variable Regions of Lead-Specific Antibodies

FIG. 2

Lead-Specific Heavy Chain Sequences

```
                                                                                                                    10                                                                                                  20                                                                                                  30                                                                 CDR1
                                                                                                                                                                                                                                                                                                                                                                            35A  36
       Asp Val Gln Leu Gln Glu Ser Gly Pro Gly Leu Val Lys Pro Ser Gln Ser Leu Thr Cys Thr Val Thr Gly Tyr Ser Ile Thr Ser Asp Tyr Ala Trp Asn Trp
13D10  GAT GTG CAG CTT CAG GAG TCG GGA CCT GGC CTG GTG AAA CCT TCT CAG TCT CTG ACC TGC ACT GTC ACT GGC TAC TCA ATC ACC AGT GAT TAT GCC TGG AAC TGG

Gln Val Gln Leu Gln Gln Ser Gly Ala Glu Leu Met Lys Pro Gly Ala Ser Val Lys Ile Ser Cys Lys Ala Thr Gly Tyr Thr Phe Ser Ser Tyr Trp Ile Glu  Trp
11D11  CAG GTT CAG CTG CAG CAG TCT GGA CCT GAG CTG ATG AAG CCT GGG GCC TCA GTG AAG ATA TCC TGC AAG GCT ACT GGC TAC ACA TTC AGT AGC TAC ATA GAG       TGG

Glu Val Gln Leu Gln Gln Ser Gly Ala Glu Leu Val Arg Ser Gly Ala Ser Val Lys Leu Ser Cys Thr Ala Ser Gly Phe Asn Ile Lys Asp Tyr Tyr Met His  Asp
14G11  GAG GTC CAG CTG CAG CAG TCT GGA GCA GAG CTT GTG AGG TCA GGG GCC TCA GTC AAG TTG TCC TGC ACA GCT TCT GGC TTC AAC ATT AAA GAC TAC TAT ATG CAC  TGG

Glu Ser Gly Gly Gly Leu Val Gln Pro Gly Gly Ser Leu Lys Leu Ser Cys Ala Ala Ser Gly Phe Thr Phe Asn Thr Tyr Ala Met Asn  Trp
6F5    GAG TCT GGT GGA GGA TTG GTG CAG CCT AAA CTC TCA TGC GCA GCC TCT GGA TTC ACC TTC AAT ACC TAC GCC ATG AAC                   TGG

Glu Val Lys Leu Glu Glu Ser Gly Gly Gly Leu Val Gln Pro Gly Gly Ser Met Lys Leu Ser Cys Val Ala Ser Gly Phe Thr Phe Ser Asn Tyr Trp Met Asn  Trp
7D10   GAA GTT AAG CTT GAG GAG TCT GGA GGA GGC TTG GTG CAA CCT GGA GGA TCC ATG AAA CTC TCT TGT GTT GCC TCT GGA TTC ACT TTC AGT AAC TAC TGG ATG AAC  TGG

Glu Val Lys Leu Thr Glu Ser Gly Gly Gly Leu Val Gln Pro Gly Gly Ser Met Lys Leu Ser Cys Val Ala Ser Gly Phe Thr Phe Ser Asn Tyr Trp Met Asn  Trp
4E8    GAA GTG AAG CTG ACT GAG TCT GGA GGA GGA TTG GTA CAG CCT CAA GGA TCC ATG AAA CTC TCC TGT GCC GCC TCT GGA TTC ACT TTC AGT AAC TAC TGG ATG AAC  TGG
```

```
                        40                                                          50  52 52A 52B                                                                                   60                                                                                                  70
                                                                                                                                                                                                                                                                                            CDR2
       Ile Arg Gln Phe Pro Gly Asn Lys Leu Glu Trp Met Gly Tyr Ile Ser                    Tyr Ser Gly Ser Thr Ser Tyr Asn Pro Ser Leu Lys Ser Arg Ile Ser Ile Thr Arg
13D10  ATC CGG CAG TTT CCA GGA AAC AAA CTG GAG TGG ATG GGC TAC ATA AGC                    TAC AGT GGT AGC ACT AGC TAC AAC CCA TCT CTC AAA AGT CGA ATC TCT ATC ACT CGA

Val Lys Gln Arg Pro Gly His Gly Leu Glu Trp Ile Gly Ile Leu Pro                    Gly Ser Gly Ser Thr Asn Tyr Asn Glu Lys Phe Lys Gly Lys Ala Thr Phe Thr Ala
11D11  GTA AAG CAG AGG CCT GGA CAT GGC CTT GAG TGG ATT GGA GAG ATT TTA CCT                GGA AGT GGT AGT ACT AAC TAC AAT GAG AAG TTC AAG GGC AAG GCC ACA TTC ACT GCA

Val Lys Gln Arg Pro Glu Gln Gly Leu Glu Trp Ile Gly Trp Ile Asp Pro                Glu Asn Gly Asp Thr Glu Tyr Ala Pro Lys Phe Gln Gly Lys Ala Thr Met Thr Ala
14G11  GTG AAG CAG AGG CCT GAA CAG GGC CTG GAG TGG ATT GGA TGG ATT GAT CCT                GAG AAT GGT GAT ACT GAA TAT GCC CCG AAG TTC CAG GGC AAG GCC ACT ATG ACT GCA

Val Arg Gln Ala Pro Gly Lys Gly Leu Glu Trp Val Ala Arg Ile Arg Ser                Lys Ser Asn Asn Tyr Ala Thr His Tyr Ala Asp Ser Val Lys Asp Arg Phe Thr Ile
6F5    GTT CGC CAG GCT CCA GGA AAG GGT TTG GAA TGG GTT GCT CGC ATA AGA AGT                AAA AGT AAT AAT TAT GCA ACA CAT TAT GCA GAC TCA GTG AAA GAC AGG TTC ACC ATC

Val Arg Gln Ser Pro Glu Lys Gly Leu Glu Trp Val Ala Glu Val Arg Leu                Lys Ser Asn Asn Tyr Ala Thr His Tyr Ala Glu Ser Val Lys Gly Arg Phe Thr Ile
7D10   GTC CGC CAG TCT CCA GAG AAG GGG CTT GAG TGG GTT GCT GAA GTT AAA TTG                AAA TCT AAT AAT TAT GCA ACA CAT TAT GCG GAG TCT GTG AAA GGG AGG TTC ACC ATC

Val Arg Gln Ser Pro Glu Lys Gly Leu Glu Trp Val Ala Glu Ile Arg Leu                Lys Ser Asn Asn Tyr Ala Thr Asn Tyr Ala Glu Ser Val Lys Gly Arg Phe Thr Ile
4E8    GTC CGC CAG TCT CCA GAG AAG GGG CTT GAG TGG GTT GCT GAA ATT AGA TTG                AAA TCT AGT AAT AAT TAT GCA ACA AAT TAT GCG GAG TCT GTG AAA GGG AGG TTC ACC ATC
```

```
       Ser  Ile Ser
13D10  ATC ACT CGA (Arg)
11D11  ATC ACT GCA (Ala)
14G11  ATG ACT GCA (Ala)
6F5    TTC ACC ATC (Ile)
7D10   TTC ACC ATC (Ile)
4E8    TTC ACC ATC (Ile)
```

FIG. 3A

Lead-Specific Heavy Chain Sequences

|  | 80 | 82 82A 82B 82C 83 | 90 | 94 | CDR3 | 103 |
|---|---|---|---|---|---|---|
| 13D10 | Asp Thr Ser Lys Asn Gln Phe Phe Leu Gln<br>GAC ACA TCC AAG AAC CAG TTC TTC CTG CAG | Leu Asn Ser Val Thr Thr Glu Asp Thr Ala<br>CTG AAT TCT GTG ACT ACT GAG GAC ACA GCC | Thr Ala Tyr Tyr Cys Ala Arg<br>ACA GCC TAT TAC TGT GCA AGA | Cys Gly Asn Tyr Pro Trp Tyr Phe Asp<br>TGT GGT AAC TAC CCG TGG TAC TTT GAC | Tyr Trp<br>TAC TGG |
| 11D11 | Asp Thr Ser Ser Asn Thr Ala Tyr Met Gln<br>GAT ACA TCC TCC AAC ACA GCC TAC ATG CAA | Val Ser Ser Leu Thr Ser Glu Asp Ser Ala<br>GTC AGC AGC CTG ACA TCT GAG GAC TCT GCC | Val Tyr Tyr Cys Ala Arg<br>GTC TAT TAC TGT GCA AGG | Ile Tyr Tyr Gly His Leu Trp Phe Ala<br>ATC TAC TAT GGT CAC TTG TGG TTT GCT | Tyr Trp<br>TAC TGG |
| 14G11 | Asp Thr Ser Asn Ile Ala Tyr Leu Gln<br>GAC ACA TCC AAT ATA GCC TAC CTG | Leu Ser Ser Leu Thr Ser Glu Asp Ser Ala<br>CTC AGC AGC CTG ACA TCT GAG GAT TCT GCC | Val Tyr Tyr Cys Asn Pro<br>GTC TAT TAC TGT AAT CCC | Tyr Gly Tyr Asp Asp Ala Met Asp<br>TAT GGT TAC GAC GAT GCT ATG GAC | Tyr Trp<br>.... TAC TGG |
| 6F5 | Ser Arg Asp Asp Ser Gln Ser Met Leu Tyr<br>TCC AGA GAT GAT TCA CAA AGC ATG CTT | Leu Gln Leu Asn Asn Leu Lys Thr Glu Asp<br>CTG CAA ATG AAC AAC TTG AAA ACT GAG | Thr Ala Met Tyr Tyr Cys Val Arg Arg<br>GAC ACA GCC ATG TAT TAC TGT GTG AGA | CGG | Phe Ala Tyr Trp<br>TTT GCT TAC TGG |
| 7D10 | Arg Asp Ser Lys Ser Ser Val Tyr Leu Gln<br>AGA GAT TCC AAA AGT AGT GTC TAC CTG | Met Asn Asn Leu Arg Ala Glu Asp Thr<br>CAA ATG AAC AAC TTA AGA GCT GAA GAC | Gly Ile Tyr Tyr Cys Thr Arg<br>GGA ATT TAT TAT TGC ACC AGA | Gly Arg Glu Gly Gly Val Ala<br>GGT TAC TGT GAG GGG GTT GCT | Tyr Trp<br>TAC TGG |
| 4E8 | Arg Asp Ser Lys Ser Ser Val Tyr Leu Gln<br>AGA GAT TCC AAA AGT AGT GTC TAC CTG | Met Asn Asn Leu Arg Ala Glu Asp Thr<br>CAA ATG AAC AAC TTA AGA GCT GAA GAC | Gly Ile Tyr Tyr Cys Thr Arg<br>GGC ATT TAT TAT TGC ACC AGA | Gly Tyr Gly Arg Glu Gly Gly Phe Ala<br>GGT TAC CGT AGA GAG GAG GGG TTT GCT | Tyr Trp<br>TAC TGG |

|  | 110 |  |
|---|---|---|
| 13D10 | Gly Gln Gly Thr Thr Leu Thr Val Ser Ser<br>GGC CAA GGC ACC ACT CTC ACA GTC TCC TCA | |
| 11D11 | Gly Gln Gly Thr Leu Val Thr Val Ser Ala<br>GGC CAA GGG ACT CTG GTC ACT GTC TCT GCA | |
| 14G11 | Gly Gln Gly Thr Ser Val Thr Val Ser Ser<br>GGA CAA GGA ACC TCA GTC ACC GTC TCC TCA | |
| 6F5 | Gly Gln Gly Thr Leu Val Thr Val Ser Ala<br>GGC CAA GGG GTC GTC ACT GTC TCT GCA | |
| 7D10 | Gly Gln Gly Thr Leu Val Thr Val Ser Ala<br>GGG CAA GGG ACT CTG GTC ACT GTC TCT GCA | |
| 4E8 | Gly Glu Gly Thr Leu Val Thr Val Ser Ala<br>(GGG)GAA GGG ACT CTG GTC ACT GTC TCT GCA<br>(GGC) | |

FIG. 3B

Lead-Specific Light Chain Sequences

```
                                      10                              20                                 CDR1
                                                                                                      30
1G05  Glu Thr Thr Val Thr Gln Ser Pro Ala Ser Leu Ser Val Ala Thr Gly Glu Lys Val Thr Ile Arg Cys Ile Thr Ser Thr Asp Ile Asp Asp Met Asn Trp Tyr Gln
      GAA ACA ACT GTG ACT CAG TCT CCA GCA TCC CTG TCC GTG GCT ACA GGA GAA AAA GTC ACT ATA AGA TGC ATA ACC AGC ACT GAT ATT GAT GAT ATG AAC TGG TAC CAG

2E7   Asp Ile Val Met Thr Gln Ser Gln Lys Phe Met Ser Thr Ser Val Gly Asp Arg Val Ser Val Thr Cys Lys Ala Ser Gln Asn Val Gly Thr Asn Val Ala Trp Tyr Gln
      GAC ATT GTG ATG ACC CAG TCT CAA AAA TTC ATG TCC ACA TCA GTA GGA GAC AGG GTC AGC GTC ACC TGC AAG GCC AGT CAG AAT GTG GGT ACT AAT GTA GCC TGG TAT CAA

7D10  Glu Thr Thr Val Thr Gln Ser Pro Ala Ser Leu Ser Val Ala Thr Gly Glu Lys Val Thr Ile Arg Cys Ile Thr Ser Thr Asp Ile Asp Asp Met Asn Trp Tyr Gln
      GAA ACA ACT GTG ACT CAG TCT CCA GCA TCC CTG TCC GTG GCT ACA GGA GAA AAA GTC ACT ATC AGA TGC ATA ACC AGC ACT GAT ATT GAT GAT ATG AAC TGG TAC CAG

CDR2
        40                              50                                  60                                  70
1G05  Gln Lys Pro Gly Glu Pro Pro Lys Leu Leu Ile Ser Glu Gly Asn Thr Leu Arg Pro Gly Val Pro Ser Arg Phe Ser Ser Ser Gly Tyr Gly Thr Asp Phe Val Phe Thr
      CAG AAG CCA GGG GAA CCT CCT AAG CTC CTT ATT TCA GAA GGC AAT ACT CTT CGT CCT GGA GTC CCA TCC CGA TTC TCC AGC AGT GGC TAT GGC ACA GAT TTT GTT TTT ACA

2E7   Gln Lys Pro Gly Gln Ser Pro Lys Ala Leu Ile Tyr Ser Ala Ser Tyr Arg Tyr Ser Gly Val Pro Asp Arg Phe Thr Gly Ser Gly Ser Gly Thr Asp Phe Thr Leu Thr
      CAG AAA CCA GGG CAA TCT CCT AAA GCA CTG ATT TAC TCG GCA TCC TAC AGG TAC AGT GGA GTC CCT GAT CGC TTC ACA GGC AGT GGA TCT GGG ACA GAT TTC ACT CTC ACC

6F5   His Trp Asn Gln Gln Lys Pro Gly Gln Pro Pro Arg Leu Leu Ile Tyr Leu Val Ser Asn Leu Glu Ser Gly Val Pro Ala Arg Phe Ser Gly Ser Gly Ser Gly Thr Asp
      CAC TGG AAC CAA CAG AAG CCA GGA CAG CCT CCT AGA CTC CTG ATC TAT CTT GTA TCC AAC CTA GAA TCT GGG GTC CCT GCC AGG TTC AGT GGC AGT GGG TCT GGG ACA GAC

7D10  Gln Lys Pro Gly Glu Pro Pro Lys Leu Leu Ile Ser Glu Gly Asn Thr Leu Arg Pro Gly Val Pro Ser Arg Phe Ser Ser Ser Gly Tyr Gly Thr Asp Phe Val Phe Thr
      CAG AAG CCA GGG GAA CCT CCT AAG CTC CTT ATT TCA GAA GGC AAT ACT CTT CGT CCT GGA GTC CCA TCC CGA TTC TCC AGC AGT GGC TAT GGC ACA GAT TTT GTT TTT ACA

CDR3
       80                              90                                 100
1G05  Ile Glu Asn Thr Leu Ser Glu Asp Val Ala Asp Tyr Tyr Cys Leu Gln Ser Asp Asn Met Pro Leu Thr Phe Gly Ala Gly Thr Lys Leu Glu Leu Lys
      ATT GAA AAC ACG CTC TCA GAA GAT GTT GCA GAT TAC TGT CTT CAA AGT GAT AAC ATG CCT CTC ACG TTC GGT GCT GGG ACC AAG CTG GAG CTG AAA

2E7   Ile Ser Asp Val Gln Ser Glu Asp Leu Ala Glu Tyr Phe Cys Gln Gln Tyr Asn Ile Tyr Pro Leu Thr Phe Gly Ala Gly Thr Lys Leu Glu Leu Lys
      ATC AGC GAT GTG CAG TCT GAA GAC TTG GCA GAG TAT TTC TGT CAA CAA TAT AAC ATC TAT CCG CTC ACG TTC GGT GCT GGG ACC AAG CTG GAG CTG AAA

7D10  Ile Glu Asn Thr Leu Ser Glu Asp Val Ala Asp Tyr Tyr Cys Leu Gln Ser Asp Asn Met Pro Phe Thr Phe Gly Ser Gly Thr Lys Leu Glu Ile Lys
      ATT GAA AAC ACG CTC TCA GAA GAT GTT GCA GAT TAC TGT CTT CAA AGT GAT AAC ATG CCA TTC ACG TTC GGC TCG GGG ACA AAG TTG GAA ATA AAA
```

2B4 heavy chain

```
                                     10                                          20
 E   V   Q   L   V   E   S   G   G   L   V   Q   P   K   G   S   L   K   L
GAG GTG CAG CTT GTT GAG TCT GGT GGA GGA TTG GTG CAG CCT AAA GGG TCA TTG AAA CTC 30                                   40
 S   C   A   A   S   G   F   T   F   N   T   Y   A   M   N   W   V   R   Q   L
TCA TGT GCA GCC TCT GGA TTC ACC TTC AAT ACC TAC GCC ATG AAC TGG GTC CGC CAG CTC 50      52  52A 52B 52C
 Q   G   K   G   L   E   W   V   A   R   I   R   S   K   S   N   N   Y   A   T
CAA GGA AAG GGT TTG GAA TGG GTT GCT CGC ATA AGA AGT AAA AGT AAT AAT TAT GCA ACA 60                                          70
 Y   Y   A   D   S   V   K   D   R   F   T   I   S   R   D   D   S   Q   S   M
TAT TAT GCC GAT TCA GTG AAA GAC AGG TTC ACC ATC TCC AGA GAT GAT TCA CAA AGC ATG 80                                          90
 L   Y   L   Q   M   N   N   L   K   T   E   D   T   A   M   Y   Y   C   V   R
CTC TAT CTG CAA ATG AAC AAC TTG AAA ACT GAG GAC ACA GCC ATG TAT TAC TGT GTG AGA 96              101                         110
 R   R                        D   Y   W   G   Q   G   T   S   V   T   V   S   S
CGG AGG ... ... ... ...     GAC TAC TGG GGT CAA GGA ACC TCA GTC ACC GTC TCC TCA
```

FIG. 6

2E7 heavy chain

| | | | | | | | | | | | | | | | | |
|---|---|---|---|---|---|---|---|---|---|---|---|---|---|---|---|---|
|Glu|Val|Lys|Leu|Val|Glu|Ser|Gly|Gly|Gly|Leu|Val|Gln|Pro|Gly|Gly|Ser|Leu|Arg|Leu
|GAG|GTG|AAG|CTG|GTG|GAG|TCT|GGA|GGA|GGC|TTG|GTA|CAG|CCT|GGG|GGT|TCT|CTG|AGA|CTC

```
Glu Val Lys Leu Val Glu Ser Gly Gly Gly Leu Val Gln Pro Gly Gly Ser Leu Arg Leu
GAG GTG AAG CTG GTG GAG TCT GGA GGA GGC TTG GTA CAG CCT GGG GGT TCT CTG AGA CTC

Ser Cys Ala Thr Ser Gly Phe Thr Phe Thr Asp Tyr Tyr Met Ser Trp Val Arg Gln Pro
TCC TGT GCA ACT TCT GGG TTC ACC TTC ACT GAT TAC TAC ATG AGC TGG GTC CGC CAG CCT

Pro Gly Lys Ala Leu Glu Trp Leu Gly Leu Ile Arg Asn Lys Ala Asn Gly Tyr Thr Thr
CCA GGA AAG GCA CTT GAG TGG TTG GGT TTG ATT AGA AAC AAA GCT AAT GGT TAC ACA ACA

Glu Tyr Ser Ala Ser Val Lys Gly Arg Phe Thr Ile Ser Arg Asp Asn Ser Gln Ser Ile
GAG TAC AGT GCA TCT GTG AAG GGT CGG TTC ACC ATC TCC AGA GAT AAT TCC CAA AGC ATC

Leu Tyr Leu Gln Met Asn Thr Leu Arg Ala Glu Asp Ser Ala Thr Tyr Tyr Cys Ala Arg
CTC TAT CTT CAA ATG AAC ACC CTG AGA GCT GAG GAC AGT GCC ACT TAT TAC TGT GCA AGA

Asp Ile Tyr Tyr Asp Tyr Asp Tyr Tyr Ala Met Asp Tyr Trp Gly Gln Gly Thr Ser Val
GAT ATC TAC TAT GAT TAC GAC TAC TAT GCT ATG GAC TAC TGG GGT CAA GGA ACC TCA GTC

Thr Val Ser Ser
ACC GTC TCC TCA
```

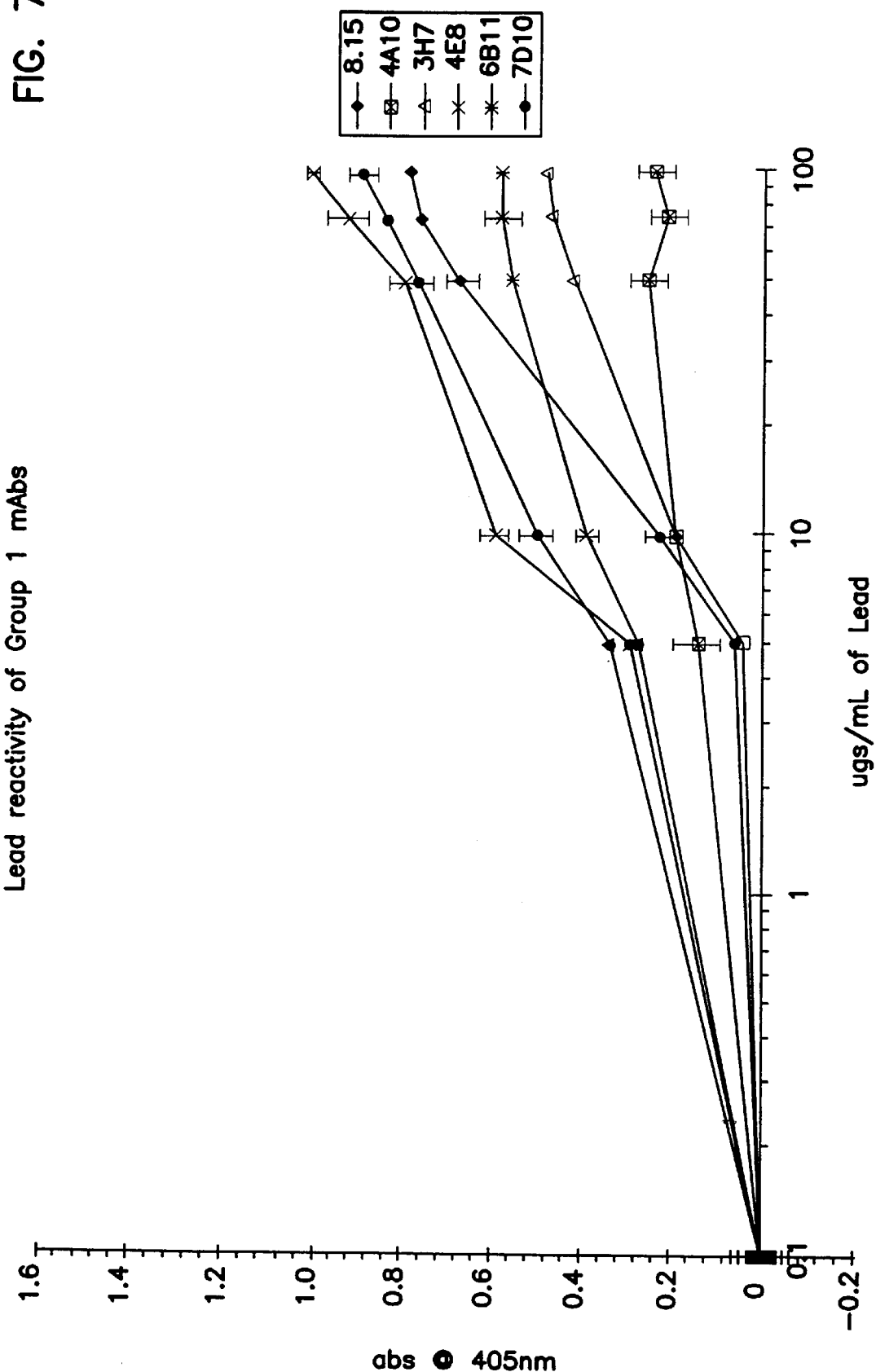

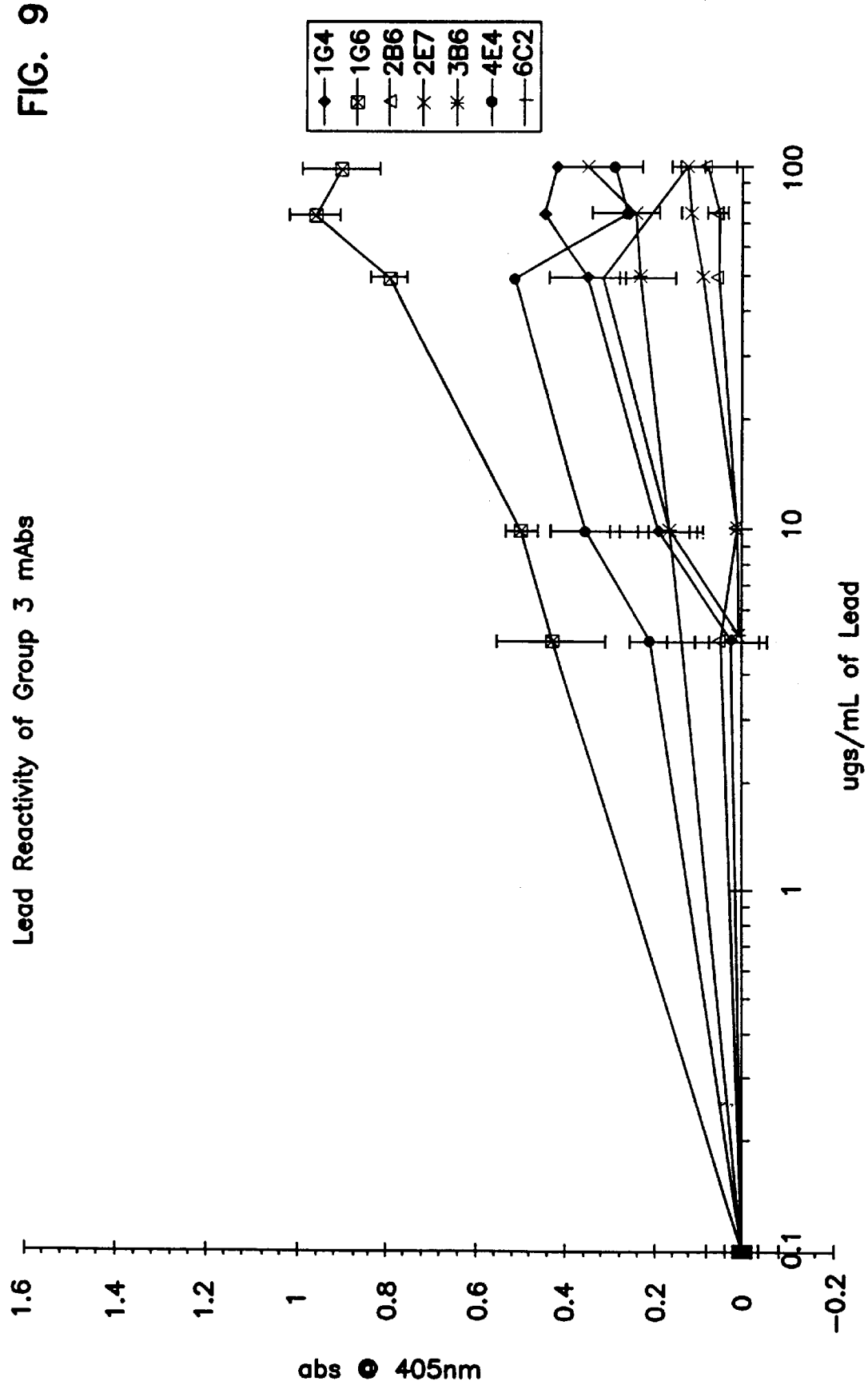

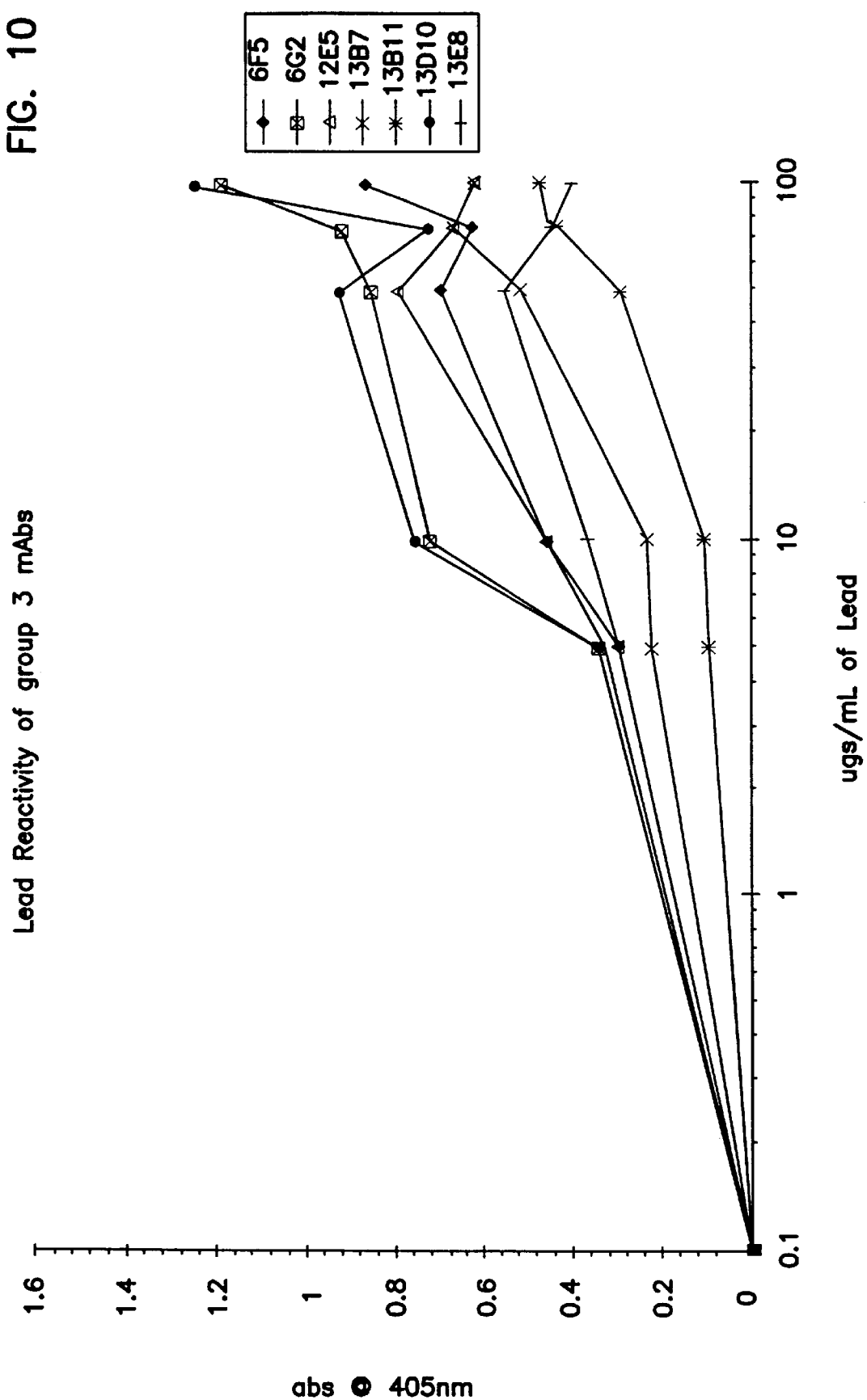

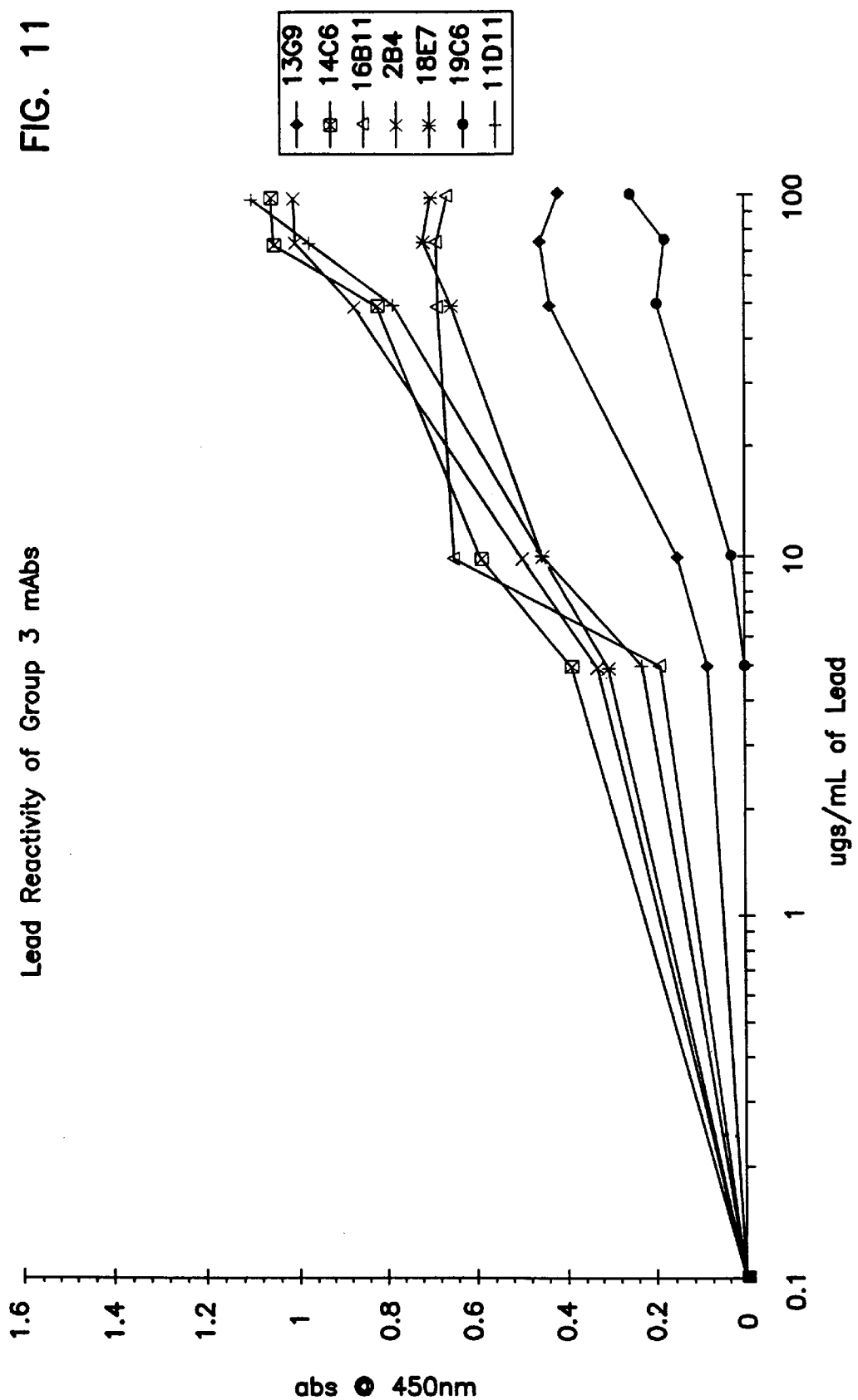

SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
      (A) LENGTH: 354 base pairs
      (B) TYPE: nucleic acid
      (C) STRANDEDNESS: single
      (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
      (A) NAME/KEY: Coding Sequence
      (B) LOCATION: 1...354
      (D) OTHER INFORMATION:

(xi) SEQUENCE DESCRIPTION: SEQ ID NO:1:

```
GAG GTT CAG CTG CAG CAG TCT GGA CCT GAG CTG GTG AGG CCT GGA CCT      48
Glu Val Gln Leu Gln Gln Ser Gly Pro Glu Leu Val Arg Pro Gly Pro
 1               5                  10                  15

TCA GTG AAG CTG TCC TGC AAG GCT TCT GGC TAC TCC TTC ACC AGC TAC      96
Ser Val Lys Leu Ser Cys Lys Ala Ser Gly Tyr Ser Phe Thr Ser Tyr
            20                  25                  30

TGG ATG AAC TGG GTG AAG CAG AGG CCT GGA CGA GGA CTT GAG TGG ATT     144
Trp Met Asn Trp Val Lys Gln Arg Pro Gly Arg Gly Leu Glu Trp Ile
        35                  40                  45

GGC ATG ATT CAT CCT TCC GAT AGT GAA ACT AGG TTA AAT CAG AAG TTC     192
Gly Met Ile His Pro Ser Asp Ser Glu Thr Arg Leu Asn Gln Lys Phe
    50                  55                  60

AAG GAC AAG GCC ACA TTG ACT GTA GAC AAA TCC TCC AGC ACA GCC TAC     240
Lys Asp Lys Ala Thr Leu Thr Val Asp Lys Ser Ser Ser Thr Ala Tyr
65                  70                  75                  80

ATG CAA CTC AGC AGC CCG ACA TCT GAG GAC TCT GCG GTC TAT TAC TGT     288
Met Gln Leu Ser Ser Pro Thr Ser Glu Asp Ser Ala Val Tyr Tyr Cys
                85                  90                  95

GCA AGA AGG GGT AAC TCC GCC TGG TTT GCT TAC TGG GGC CAA GGG ACT     336
Ala Arg Arg Gly Asn Ser Ala Trp Phe Ala Tyr Trp Gly Gln Gly Thr
            100                 105                 110

CTG GTC ACT GTC TCT GCA                                             354
Leu Val Thr Val Ser Ala
        115
```

(2) INFORMATION FOR SEQ ID NO:2:

(i) SEQUENCE CHARACTERISTICS:
      (A) LENGTH: 118 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:2:

```
Glu Val Gln Leu Gln Gln Ser Gly Pro Glu Leu Val Arg Pro Gly Pro
 1               5                  10                  15

Ser Val Lys Leu Ser Cys Lys Ala Ser Gly Tyr Ser Phe Thr Ser Tyr
             20                  25                  30

Trp Met Asn Trp Val Lys Gln Arg Pro Gly Arg Gly Leu Glu Trp Ile
         35                  40                  45

Gly Met Ile His Pro Ser Asp Ser Glu Thr Arg Leu Asn Gln Lys Phe
     50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
             85                  90                  95

Ala Arg Arg Gly Asn Ser Ala Trp Phe Ala Tyr Trp Gly Gln Gly Thr
            100                 105                 110

Leu Val Thr Val Ser Ala
            115
```

(2) INFORMATION FOR SEQ ID NO:3:

(i) SEQUENCE CHARACTERISTICS:
        (A) LENGTH: 366 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...366
        (D) OTHER INFORMATION:

(xi) SEQUENCE DESCRIPTION: SEQ ID NO:3:

```
CAG GTC CAG CTG CAG CAG TCT GGA GCT GGG CTG GTG AAA CCC GGG GCA        48
Gln Val Gln Leu Gln Gln Ser Gly Ala Gly Leu Val Lys Pro Gly Ala
 1               5                  10                  15

TCA GTG AAG CTG TCC TGC AAG GCT TCT GGC TAC ACC TTC ACT GAG TAT        96
Ser Val Lys Leu Ser Cys Lys Ala Ser Gly Tyr Thr Phe Thr Glu Tyr
             20                  25                  30

ATT ATA CAC TGG GTA AAG CAG AGG TCT GGA CAG GGT CTT GAG TGG ATT       144
Ile Ile His Trp Val Lys Gln Arg Ser Gly Gln Gly Leu Glu Trp Ile
         35                  40                  45

GGG TGG TTT TAC CCT GGA AGT GGT AGT ATA AAG TAC AAT GAG AAA TTC       192
Gly Trp Phe Tyr Pro Gly Ser Gly Ser Ile Lys Tyr Asn Glu Lys Phe
     50                  55                  60

AAG GAC AAG GCC ACA TTG ACT GCG GAC AAA TCC TCC AGC ACA GTC TAT       240
Lys Asp Lys Ala Thr Leu Thr Ala Asp Lys Ser Ser Ser Thr Val Tyr
65                  70                  75                  80

ATG GAG CTT AGT AGA TTG ACA TCT GAA GAC TCT GCG GTC TAT TTC TGT       288
Met Glu Leu Ser Arg Leu Thr Ser Glu Asp Ser Ala Val Tyr Phe Cys
```

|  | | 85 | | | | 90 | | | | 95 | | | |  |
|---|---|---|---|---|---|---|---|---|---|---|---|---|---|---|

```
GCA AGA CAC GAA GGG TAT GGT AAC TAC GTG GCC TGG TTT GCT TAC TGG     336
Ala Arg His Glu Gly Tyr Gly Asn Tyr Val Ala Trp Phe Ala Tyr Trp
            100                 105                 110

GGC CAA GGG ACT CTG GTC ACT GTC TCT GCA                             366
Gly Gln Gly Thr Leu Val Thr Val Ser Ala
            115                 120
```

(2) INFORMATION FOR SEQ ID NO:4:

(i) SEQUENCE CHARACTERISTICS:
        (A) LENGTH: 122 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:4:

```
Gln Val Gln Leu Gln Gln Ser Gly Ala Gly Leu Val Lys Pro Gly Ala
 1               5                  10                  15

Ser Val Lys Leu Ser Cys Lys Ala Ser Gly Tyr Thr Phe Thr Glu Tyr
            20                  25                  30

Ile Ile His Trp Val Lys Gln Arg Ser Gly Gln Gly Leu Glu Trp Ile
            35                  40                  45

Gly Trp Phe Tyr Pro Gly Ser Gly Ser Ile Lys Tyr Asn Glu Lys Phe
    50                  55                  60

Lys Asp Lys Ala Thr Leu Thr Ala Asp Lys Ser Ser Ser Thr Val Tyr
65                  70                  75                  80

Met Glu Leu Ser Arg Leu Thr Ser Glu Asp Ser Ala Val Tyr Phe Cys
                85                  90                  95

Ala Arg His Glu Gly Tyr Gly Asn Tyr Val Ala Trp Phe Ala Tyr Trp
            100                 105                 110

Gly Gln Gly Thr Leu Val Thr Val Ser Ala
            115                 120
```

(2) INFORMATION FOR SEQ ID NO:5:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...357
        (D) OTHER INFORMATION:

(xi) SEQUENCE DESCRIPTION: SEQ ID NO:5:

```
GAG GTC CAG CTG CAG CAG TCT GGG GCT GAG CTT GTG AAG CCT GGG GCT        48
Glu Val Gln Leu Gln Gln Ser Gly Ala Glu Leu Val Lys Pro Gly Ala
 1               5                  10                  15

CCA GTG AAG CTG TCC TGC AAG GCT TCT GGC TAC ACC TTC ACC AGC TAC        96
Pro Val Lys Leu Ser Cys Lys Ala Ser Gly Tyr Thr Phe Thr Ser Tyr
            20                  25                  30

TGG ATG AAC TGG GTG AAG CAG AGG CCT GGA CGA GGC CTC GAG TGG ATT       144
Trp Met Asn Trp Val Lys Gln Arg Pro Gly Arg Gly Leu Glu Trp Ile
        35                  40                  45

GGA AGG ATT GAT CCT TCC GAT AGT GAA ACT CAC TAC AAT CAA AAG TTC       192
Gly Arg Ile Asp Pro Ser Asp Ser Glu Thr His Tyr Asn Gln Lys Phe
 50                  55                  60

AAG GAC AAG GCC ACA CTG ACT GTA GAC AAA TCC TCC AGC ACA GCC TAC       240
Lys Asp Lys Ala Thr Leu Thr Val Asp Lys Ser Ser Ser Thr Ala Tyr
 65                  70                  75                  80

ATC CAA CTC AGC AGC CTG ACA TCT GAG GAC TCT GCG GTC TAT TAC TGT       288
Ile Gln Leu Ser Ser Leu Thr Ser Glu Asp Ser Ala Val Tyr Tyr Cys
                85                  90                  95

GCA AGA CAT CAC TAC GGC TAC TAT GCT ATG GAC TAC TGG GGT CAA GGA       336
Ala Arg His His Tyr Gly Tyr Tyr Ala Met Asp Tyr Trp Gly Gln Gly
                100                 105                 110

ACC TCA GTC ACC GTC TCC TCA                                            357
Thr Ser Val Thr Val Ser Ser
            115
```

(2) INFORMATION FOR SEQ ID NO:6:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:6:

```
Glu Val Gln Leu Gln Gln Ser Gly Ala Glu Leu Val Lys Pro Gly Ala
 1               5                  10                  15

Pro Val Lys Leu Ser Cys Lys Ala Ser Gly Tyr Thr Phe Thr Ser Tyr
            20                  25                  30

Trp Met Asn Trp Val Lys Gln Arg Pro Gly Arg Gly Leu Glu Trp Ile
        35                  40                  45

Gly Arg Ile Asp Pro Ser Asp Ser Glu Thr His Tyr Asn Gln Lys Phe
 50                  55                  60

Lys Asp Lys Ala Thr Leu Thr Val Asp Lys Ser Ser Ser Thr Ala Tyr
 65                  70                  75                  80

Ile Gln Leu Ser Ser Leu Thr Ser Glu Asp Ser Ala Val Tyr Tyr Cys
                85                  90                  95

Ala Arg His His Tyr Gly Tyr Tyr Ala Met Asp Tyr Trp Gly Gln Gly
                100                 105                 110

Thr Ser Val Thr Val Ser Ser
            115
```

(2) INFORMATION FOR SEQ ID NO:7:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...354
        (D) OTHER INFORMATION:

(xi) SEQUENCE DESCRIPTION: SEQ ID NO:7:

```
GAG GTC CAG CTG CAG CAG TCT GGG GCT GAG CTG GTG AGG CCT GGA GCT      48
Glu Val Gln Leu Gln Gln Ser Gly Ala Glu Leu Val Arg Pro Gly Ala
 1               5                  10                  15

TCA GTG AAG CTG TCC TGC AAG GCT TCT GGC TAC TCC TTC ACC AGC TAC      96
Ser Val Lys Leu Ser Cys Lys Ala Ser Gly Tyr Ser Phe Thr Ser Tyr
             20                  25                  30

TGG ATG AAC TGG GTG AAG CAG AGG CCT GGA CAA GGC CTT GAG TGG ATT     144
Trp Met Asn Trp Val Lys Gln Arg Pro Gly Gln Gly Leu Glu Trp Ile
         35                  40                  45

GGC ATG ATT CAT CCT TCC GAT AGT GAA ACT AGG TTA AAT CAG AAG TTC     192
Gly Met Ile His Pro Ser Asp Ser Glu Thr Arg Leu Asn Gln Lys Phe
 50                  55                  60

AAG GAC AAG GCC ACA TTG ACT GTA GAC AAA TCC TCC AGC ACA GCC TAC     240
Lys Asp Lys Ala Thr Leu Thr Val Asp Lys Ser Ser Ser Thr Ala Tyr
 65                  70                  75                  80

ATG CAA CTC AGC AGC CCG ACA TCT GAG GAC TCT GCG GTC TAT TAC TGT     288
Met Gln Leu Ser Ser Pro Thr Ser Glu Asp Ser Ala Val Tyr Tyr Cys
             85                  90                  95

GCA AGA AGG AGG GAT TAC GAC CCG TTT GCT TAC TGG GGC CAA GGG ACT     336
Ala Arg Arg Arg Asp Tyr Asp Pro Phe Ala Tyr Trp Gly Gln Gly Thr
            100                 105                 110

CTG GTC ACT GTC TCT GCA                                              354
Leu Val Thr Val Ser Ala
            115
```

(2) INFORMATION FOR SEQ ID NO:8:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:8:

```
Glu Val Gln Leu Gln Gln Ser Gly Ala Glu Leu Val Arg Pro Gly Ala
 1               5                  10                 15

Ser Val Lys Leu Ser Cys Lys Ala Ser Gly Tyr Ser Phe Thr Ser Tyr
             20                  25                 30

Trp Met Asn Trp Val Lys Gln Arg Pro Gly Gln Gly Leu Glu Trp Ile
         35                  40                  45

Gly Met Ile His Pro Ser Asp Ser Glu Thr Arg Leu Asn Gln Lys Phe
     50                  55                  60

Lys Asp Lys Ala Thr Leu Thr Val Asp Lys Ser Ser Ser Thr Ala Tyr
 65                  70                  75                  80

Met Gln Leu Ser Ser Pro Thr Ser Glu Asp Ser Ala Val Tyr Tyr Cys
             85                  90                  95

Ala Arg Arg Arg Asp Tyr Asp Pro Phe Ala Tyr Trp Gly Gln Gly Thr
            100                 105                 110

Leu Val Thr Val Ser Ala
            115
```

(2) INFORMATION FOR SEQ ID NO:9:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...357
        (D) OTHER INFORMATION:

(xi) SEQUENCE DESCRIPTION: SEQ ID NO:9:

```
GAG GTC CAG CTG CAG CAG TCT GGA GCT GAG CTG GTA AGG CCT GGG ACT        48
Glu Val Gln Leu Gln Gln Ser Gly Ala Glu Leu Val Arg Pro Gly Thr
 1               5                  10                  15

TCA GTG AAG GTG TCC TGC AAG GCT TCT GGA TAC GCC TTC ACT AAT TAC        96
Ser Val Lys Val Ser Cys Lys Ala Ser Gly Tyr Ala Phe Thr Asn Tyr
             20                  25                  30

TTG ATA GAG TGG GTA AAG CAG AGG CCT GGA CAG GGC CTT GAG TGG ATT       144
Leu Ile Glu Trp Val Lys Gln Arg Pro Gly Gln Gly Leu Glu Trp Ile
         35                  40                  45

GGA GTG ATT AAT CCT GGA AGT GGT GGT ACT AAC TAC AAT GAG AAG TTC       192
Gly Val Ile Asn Pro Gly Ser Gly Gly Thr Asn Tyr Asn Glu Lys Phe
     50                  55                  60

AAG GGC AAG GCA ACA CTG ACT GCA GAC AAA TCC TCC AGC ACT GCC TAC       240
Lys Gly Lys Ala Thr Leu Thr Ala Asp Lys Ser Ser Ser Thr Ala Tyr
 65                  70                  75                  80

ATG CAG CTC AGC AGC CTG ACA TCT GAT GAC TCT GCG GTC TAT TTC TGT       288
Met Gln Leu Ser Ser Leu Thr Ser Asp Asp Ser Ala Val Tyr Phe Cys
             85                  90                  95

GCA AGA AGC GGC TAC GGC CAC TGG TAC TTC GAT GTC TGG GGC GCA GGG       336
Ala Arg Ser Gly Tyr Gly His Trp Tyr Phe Asp Val Trp Gly Ala Gly
            100                 105                 110

ACC ACG GTC ACC GTC TCC TCA                                           357
```

```
Thr Thr Val Thr Val Ser Ser
        115

(2) INFORMATION FOR SEQ ID NO:10:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:10:

Glu Val Gln Leu Gln Gln Ser Gly Ala Glu Leu Val Arg Pro Gly Thr
 1               5                  10                  15

Ser Val Lys Val Ser Cys Lys Ala Ser Gly Tyr Ala Phe Thr Asn Tyr
                20                  25                  30

Leu Ile Glu Trp Val Lys Gln Arg Pro Gly Gln Gly Leu Glu Trp Ile
            35                  40                  45

Gly Val Ile Asn Pro Gly Ser Gly Gly Thr Asn Tyr Asn Glu Lys Phe
        50                  55                  60

Lys Gly Lys Ala Thr Leu Thr Ala Asp Lys Ser Ser Thr Ala Tyr
 65                 70                  75                  80

Met Gln Leu Ser Ser Leu Thr Ser Asp Asp Ser Ala Val Tyr Phe Cys
                85                  90                  95

Ala Arg Ser Gly Tyr Gly His Trp Tyr Phe Asp Val Trp Gly Ala Gly
               100                 105                 110

Thr Thr Val Thr Val Ser Ser
        115

(2) INFORMATION FOR SEQ ID NO:11:

(i) SEQUENCE CHARACTERISTICS:
        (A) LENGTH: 312 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...312
        (D) OTHER INFORMATION:

(xi) SEQUENCE DESCRIPTION: SEQ ID NO:11:

ACC CAG TCT CCA TCA TCC CTG TCC ATG GCT ATA GGA GAA AAA GTC ACC       48
Thr Gln Ser Pro Ser Ser Leu Ser Met Ala Ile Gly Glu Lys Val Thr
 1               5                  10                  15

ATC AGA TGC ATA ACC AGC ACT GAT ATT GAT GAT GAT ATG AAC TGG TAC       96
```

```
Ile Arg Cys Ile Thr Ser Thr Asp Ile Asp Asp Asp Met Asn Trp Tyr
            20                  25                  30

CAG CAG AAG CCA GGG GAA CCT CCT AAA CTC CTT ATT TCA GAA GGC AAT        144
Gln Gln Lys Pro Gly Glu Pro Pro Lys Leu Leu Ile Ser Glu Gly Asn
        35                  40                  45

ACT CTT CGT CCT GGA GTC CCA TCC CGA TTC TCC AGC AGT GGC TAT GGT        192
Thr Leu Arg Pro Gly Val Pro Ser Arg Phe Ser Ser Ser Gly Tyr Gly
 50                  55                  60

ACA GAT TTT GTT TTT ACA ATT GAA AAC ATG CTC TCA GAA GAT GTT GCA        240
Thr Asp Phe Val Phe Thr Ile Glu Asn Met Leu Ser Glu Asp Val Ala
65                  70                  75                  80

GAT TAC TAC TGT TTG CAA AGT GAT AAC TTG CCT CTC ACG TTC GGA GGG        288
Asp Tyr Tyr Cys Leu Gln Ser Asp Asn Leu Pro Leu Thr Phe Gly Gly
                85                  90                  95

GGG ACC AAG CTG GAA ATA AAA CGG                                        312
Gly Thr Lys Leu Glu Ile Lys Arg
            100
```

(2) INFORMATION FOR SEQ ID NO:12:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:12:

```
Thr Gln Ser Pro Ser Ser Leu Ser Met Ala Ile Gly Glu Lys Val Thr
 1               5                  10                  15

Ile Arg Cys Ile Thr Ser Thr Asp Ile Asp Asp Asp Met Asn Trp Tyr
            20                  25                  30

Gln Gln Lys Pro Gly Glu Pro Pro Lys Leu Leu Ile Ser Glu Gly Asn
        35                  40                  45

Thr Leu Arg Pro Gly Val Pro Ser Arg Phe Ser Ser Ser Gly Tyr Gly
 50                  55                  60

Thr Asp Phe Val Phe Thr Ile Glu Asn Met Leu Ser Glu Asp Val Ala
65                  70                  75                  80

Asp Tyr Tyr Cys Leu Gln Ser Asp Asn Leu Pro Leu Thr Phe Gly Gly
                85                  90                  95

Gly Thr Lys Leu Glu Ile Lys Arg
            100
```

(2) INFORMATION FOR SEQ ID NO:13:

(i) SEQUENCE CHARACTERISTICS:
        (A) LENGTH: 312 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
    (A) NAME/KEY: Coding Sequence
    (B) LOCATION: 1...312
    (D) OTHER INFORMATION:

(xi) SEQUENCE DESCRIPTION: SEQ ID NO:13:

```
ACC CAG TCT CCA TCA TCC CTG TCC ATG GCT ATA GGA GAA AAA GTC ACC      48
Thr Gln Ser Pro Ser Ser Leu Ser Met Ala Ile Gly Glu Lys Val Thr
 1               5                  10                  15

ATC AGA TGC ATA ACC AGC ACT GAT ATT GAT GAT GAT ATG AAC TGG TAC      96
Ile Arg Cys Ile Thr Ser Thr Asp Ile Asp Asp Asp Met Asn Trp Tyr
                20                  25                  30

CAG CAG AAG CCA GGG GAA CCT CCT AAA CTC CTT ATT TCA GAA GGC AAT     144
Gln Gln Lys Pro Gly Glu Pro Pro Lys Leu Leu Ile Ser Glu Gly Asn
            35                  40                  45

ACT CTT CGT CCT GGA GTC CCA TCC CGA TTC TCC AGC AGT GGC TAT GGT     192
Thr Leu Arg Pro Gly Val Pro Ser Arg Phe Ser Ser Ser Gly Tyr Gly
 50                  55                  60

ACA GAT TTT GTT TTT ACA ATT GAA AAC ATG CTC TCA GAA GAT GTT GCA     240
Thr Asp Phe Val Phe Thr Ile Glu Asn Met Leu Ser Glu Asp Val Ala
65                  70                  75                  80

GAT TAC TAC TGT TTG CAA AGT GAT AAC TTG CCT CTC ACG TTC GGT GCT     288
Asp Tyr Tyr Cys Leu Gln Ser Asp Asn Leu Pro Leu Thr Phe Gly Ala
                85                  90                  95

GGG ACC AAG CTG GAG CTG AAA GGG                                     312
Gly Thr Lys Leu Glu Leu Lys Gly
               100
```

(2) INFORMATION FOR SEQ ID NO:14:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:14:

```
Thr Gln Ser Pro Ser Ser Leu Ser Met Ala Ile Gly Glu Lys Val Thr
 1               5                  10                  15

Ile Arg Cys Ile Thr Ser Thr Asp Ile Asp Asp Asp Met Asn Trp Tyr
                20                  25                  30

Gln Gln Lys Pro Gly Glu Pro Pro Lys Leu Leu Ile Ser Glu Gly Asn
            35                  40                  45

Thr Leu Arg Pro Gly Val Pro Ser Arg Phe Ser Ser Ser Gly Tyr Gly
 50                  55                  60

Thr Asp Phe Val Phe Thr Ile Glu Asn Met Leu Ser Glu Asp Val Ala
65                  70                  75                  80

Asp Tyr Tyr Cys Leu Gln Ser Asp Asn Leu Pro Leu Thr Phe Gly Ala
                85                  90                  95
```

```
Gly Thr Lys Leu Glu Leu Lys Gly
            100
```

(2) INFORMATION FOR SEQ ID NO:15:

(i) SEQUENCE CHARACTERISTICS:
        (A) LENGTH: 312 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...312
        (D) OTHER INFORMATION:

(xi) SEQUENCE DESCRIPTION: SEQ ID NO:15:

```
ACC CAG TCT CCA GCA TCC CTG TCC ATG GCT ATA GGA GAA AAA GTC ACC         48
Thr Gln Ser Pro Ala Ser Leu Ser Met Ala Ile Gly Glu Lys Val Thr
  1               5                  10                  15

ATC AGA TGC ATA ACC AGC ACT GAT ATT GAT GAT GAT ATG AAC TGG TAC         96
Ile Arg Cys Ile Thr Ser Thr Asp Ile Asp Asp Asp Met Asn Trp Tyr
                 20                  25                  30

CAG CAG AAG CCA GGG GAA CCT CCT AAG CTC CTT ATT TCA GAA GGC AAT        144
Gln Gln Lys Pro Gly Glu Pro Pro Lys Leu Leu Ile Ser Glu Gly Asn
             35                  40                  45

ACT CTT CGT CCT GGA GTC CCA TCC CGA TTC TCC AGC AGT GGC TAT GGT        192
Thr Leu Arg Pro Gly Val Pro Ser Arg Phe Ser Ser Ser Gly Tyr Gly
         50                  55                  60

ACA GAT TTT GTT TTT ACA ATT GAA AAC ATG CTC TCA GAA GAT GTT GCA        240
Thr Asp Phe Val Phe Thr Ile Glu Asn Met Leu Ser Glu Asp Val Ala
 65                  70                  75                  80

GAT TAC TAC TGT TTG CAA AGT GAT AAC TTG CCG CTC ACG TTC GGT GCT        288
Asp Tyr Tyr Cys Leu Gln Ser Asp Asn Leu Pro Leu Thr Phe Gly Ala
                 85                  90                  95

GGG ACC AAG CTG GAG CTG AAA CGG                                        312
Gly Thr Lys Leu Glu Leu Lys Arg
            100
```

(2) INFORMATION FOR SEQ ID NO:16:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:16:

Thr Gln Ser Pro Ala Ser Leu Ser Met Ala Ile Gly Glu Lys Val Thr

```
            1               5                   10                  15
          Ile Arg Cys Ile Thr Ser Thr Asp Ile Asp Asp Met Asn Trp Tyr
                          20                  25                  30

Gln Gln Lys Pro Gly Glu Pro Pro Lys Leu Leu Ile Ser Glu Gly Asn
                      35                  40                  45

Thr Leu Arg Pro Gly Val Pro Ser Arg Phe Ser Ser Ser Gly Tyr Gly
                  50                  55                  60

Thr Asp Phe Val Phe Thr Ile Glu Asn Met Leu Ser Glu Asp Val Ala
          65                  70                  75                  80

Asp Tyr Tyr Cys Leu Gln Ser Asp Asn Leu Pro Leu Thr Phe Gly Ala
                          85                  90                  95

Gly Thr Lys Leu Glu Leu Lys Arg
                          100
```

(2) INFORMATION FOR SEQ ID NO:17:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...357
        (D) OTHER INFORMATION:

(xi) SEQUENCE DESCRIPTION: SEQ ID NO:17:

```
GAT GTG CAG CTT CAG GAG TCG GGA CCT GGC CTG GTG AAA CCT TCT CAG        48
Asp Val Gln Leu Gln Glu Ser Gly Pro Gly Leu Val Lys Pro Ser Gln
 1               5                  10                  15

TCT CTG TCC CTC ACC TGC ACT GTC ACT GGC TAC TCA ATC ACC AGT GAT        96
Ser Leu Ser Leu Thr Cys Thr Val Thr Gly Tyr Ser Ile Thr Ser Asp
                 20                  25                  30

TAT GCC TGG AAC TGG ATC CGG CAG TTT CCA GGA AAC AAA CTG GAG TGG       144
Tyr Ala Trp Asn Trp Ile Arg Gln Phe Pro Gly Asn Lys Leu Glu Trp
             35                  40                  45

ATG GGC TAC ATA AGC TAC AGT GGT AGC ACT AGC TAC AAC CCA TCT CTC       192
Met Gly Tyr Ile Ser Tyr Ser Gly Ser Thr Ser Tyr Asn Pro Ser Leu
         50                  55                  60

AAA AGT CGA ATC TCT ATC ACT CGA GAC ACA TCC AAG AAC CAG TTC TTC       240
Lys Ser Arg Ile Ser Ile Thr Arg Asp Thr Ser Lys Asn Gln Phe Phe
 65                  70                  75                  80

CTG CAG TTG AAT TCT GTG ACT ACT GAG GAC ACA GCC ACA TAT TAC TGT       288
Leu Gln Leu Asn Ser Val Thr Thr Glu Asp Thr Ala Thr Tyr Tyr Cys
                     85                  90                  95

GCA AGA TGT GGT AAC TAC CCG TGG TAC TTT GAC TAC TGG GGC CAA GGC       336
Ala Arg Cys Gly Asn Tyr Pro Trp Tyr Phe Asp Tyr Trp Gly Gln Gly
                 100                 105                 110

ACC ACT CTC ACA GTC TCC TCA                                           357
Thr Thr Leu Thr Val Ser Ser
             115
```

(2) INFORMATION FOR SEQ ID NO:18:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:18:

```
Asp Val Gln Leu Gln Glu Ser Gly Pro Gly Leu Val Lys Pro Ser Gln
  1               5                  10                  15

Ser Leu Ser Leu Thr Cys Thr Val Thr Gly Tyr Ser Ile Thr Ser Asp
                 20                  25                  30

Tyr Ala Trp Asn Trp Ile Arg Gln Phe Pro Gly Asn Lys Leu Glu Trp
             35                  40                  45

Met Gly Tyr Ile Ser Tyr Ser Gly Ser Thr Ser Tyr Asn Pro Ser Leu
 50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Ala Arg Cys Gly Asn Tyr Pro Tyr Phe Asp Tyr Trp Gly Gln Gly
             100                 105                 110

Thr Thr Leu Thr Val Ser Ser
        115
```

(2) INFORMATION FOR SEQ ID NO:19:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...357
        (D) OTHER INFORMATION:

(xi) SEQUENCE DESCRIPTION: SEQ ID NO:19:

```
CAG GTT CAG CTG CAG CAG TCT GGA GTT GAG CTG ATG AAG CCT GGG GCC        48
Gln Val Gln Leu Gln Gln Ser Gly Val Glu Leu Met Lys Pro Gly Ala
  1               5                  10                  15

TCA GTG AAG ATA TCC TGC AAG GCT ACT GGC TAC ACA TTC AGT AGC TAC        96
Ser Val Lys Ile Ser Cys Lys Ala Thr Gly Tyr Thr Phe Ser Ser Tyr
                 20                  25                  30

TGG ATA GAG TGG GTA AAG CAG AGG CCT GGA CAT GGC CTT GAG TGG ATT       144
```

```
Trp Ile Glu Trp Val Lys Gln Arg Pro Gly His Gly Leu Glu Trp Ile
         35                  40                  45

GGA GAG ATT TTA CCT GGA AGT GGT AGT ACT AAC TAC AAT GAG AAG TTC      192
Gly Glu Ile Leu Pro Gly Ser Gly Ser Thr Asn Tyr Asn Glu Lys Phe
 50                      55                  60

AAG GGC AAG GCC ACA TTC ACT GCA GAT ACA TCC TCC AAC ACA GCC TAC      240
Lys Gly Lys Ala Thr Phe Thr Ala Asp Thr Ser Ser Asn Thr Ala Tyr
 65                  70                  75                  80

ATG CAA GTC AGC AGC CTG ACA TCT GAG GAC TCT GCC GTC TAT TAC TGT      288
Met Gln Val Ser Ser Leu Thr Ser Glu Asp Ser Ala Val Tyr Tyr Cys
                 85                  90                  95

GCA AGG ATC TAC TAT GGT CAC TTG TGG TTT GCT TAC TGG GGC CAA GGG      336
Ala Arg Ile Tyr Tyr Gly His Leu Trp Phe Ala Tyr Trp Gly Gln Gly
             100                 105                 110

ACT CTG GTC ACT GTC TCT GCA                                          357
Thr Leu Val Thr Val Ser Ala
         115
```

(2) INFORMATION FOR SEQ ID NO:20:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:20:

```
Gln Val Gln Leu Gln Gln Ser Gly Val Glu Leu Met Lys Pro Gly Ala
 1               5                  10                  15

Ser Val Lys Ile Ser Cys Lys Ala Thr Gly Tyr Thr Phe Ser Ser Tyr
             20                  25                  30

Trp Ile Glu Trp Val Lys Gln Arg Pro Gly His Gly Leu Glu Trp Ile
         35                  40                  45

Gly Glu Ile Leu Pro Gly Ser Gly Ser Thr Asn Tyr Asn Glu Lys Phe
 50                      55                  60

Lys Gly Lys Ala Thr Phe Thr Ala Asp Thr Ser Ser Asn Thr Ala Tyr
 65                  70                  75                  80

Met Gln Val Ser Ser Leu Thr Ser Glu Asp Ser Ala Val Tyr Tyr Cys
                 85                  90                  95

Ala Arg Ile Tyr Tyr Gly His Leu Trp Phe Ala Tyr Trp Gly Gln Gly
             100                 105                 110

Thr Leu Val Thr Val Ser Ala
         115
```

(2) INFORMATION FOR SEQ ID NO:21:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
    (A) NAME/KEY: Coding Sequence
    (B) LOCATION: 1...354
    (D) OTHER INFORMATION:

(xi) SEQUENCE DESCRIPTION: SEQ ID NO:21:

```
GAG GTC CAG CTG CAG CAG TCT GGG GCA GAG CTT GTG AGG TCA GGG GCC      48
Glu Val Gln Leu Gln Gln Ser Gly Ala Glu Leu Val Arg Ser Gly Ala
  1               5                  10                  15

TCA GTC AAG TTG TCC TGC ACA GCT TCT GGC TTC AAC ATT AAA GAC TAC      96
Ser Val Lys Leu Ser Cys Thr Ala Ser Gly Phe Asn Ile Lys Asp Tyr
             20                  25                  30

TAT ATG CAC TGG GTG AAG CAG AGG CCT GAA CAG GGC CTG GAG TGG ATT     144
Tyr Met His Trp Val Lys Gln Arg Pro Glu Gln Gly Leu Glu Trp Ile
         35                  40                  45

GGA TGG ATT GAT CCT GAG AAT GGT GAT ACT GAA TAT GAC CCG AAG TTC     192
Gly Trp Ile Asp Pro Glu Asn Gly Asp Thr Glu Tyr Asp Pro Lys Phe
 50                  55                  60

CAG GGC AAG GCC ACT ATG ACT GCA GAC ACA TCC TCC AAT ATA GCC TAC     240
Gln Gly Lys Ala Thr Met Thr Ala Asp Thr Ser Ser Asn Ile Ala Tyr
 65                  70                  75                  80

CTG CAG CTC AGC AGC CTG ACA TCT GAG GAT ACT GCC GTC TAT TAC TGT     288
Leu Gln Leu Ser Ser Leu Thr Ser Glu Asp Thr Ala Val Tyr Tyr Cys
                 85                  90                  95

AAT CCC TAT GGT TAC GAC GAT GCT ATG GAC TAC TGG GGA CAA GGA ACC     336
Asn Pro Tyr Gly Tyr Asp Asp Ala Met Asp Tyr Trp Gly Gln Gly Thr
            100                 105                 110

TCA GTC ACC GTC TCC TCA                                             354
Ser Val Thr Val Ser Ser
            115
```

(2) INFORMATION FOR SEQ ID NO:22:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:22:

```
Glu Val Gln Leu Gln Gln Ser Gly Ala Glu Leu Val Arg Ser Gly Ala
  1               5                  10                  15

Ser Val Lys Leu Ser Cys Thr Ala Ser Gly Phe Asn Ile Lys Asp Tyr
             20                  25                  30

Tyr Met His Trp Val Lys Gln Arg Pro Glu Gln Gly Leu Glu Trp Ile
         35                  40                  45

Gly Trp Ile Asp Pro Glu Asn Gly Asp Thr Glu Tyr Asp Pro Lys Phe
 50                  55                  60
```

```
Gln Gly Lys Ala Thr Met Thr Ala Asp Thr Ser Ser Asn Ile Ala Tyr
 65                  70                  75                  80

Leu Gln Leu Ser Ser Leu Thr Ser Glu Asp Thr Ala Val Tyr Tyr Cys
                 85                  90                  95

Asn Pro Tyr Gly Tyr Asp Asp Ala Met Asp Tyr Trp Gly Gln Gly Thr
            100                 105                 110

Ser Val Thr Val Ser Ser
        115
```

(2) INFORMATION FOR SEQ ID NO:23:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...330
        (D) OTHER INFORMATION:

(xi) SEQUENCE DESCRIPTION: SEQ ID NO:23:

```
GAG TCT GGT GGA GGA TTG GTG CAG CCT AAA GGG TCA TTG AAA CTC TCA        48
Glu Ser Gly Gly Gly Leu Val Gln Pro Lys Gly Ser Leu Lys Leu Ser
 1               5                  10                  15

TGT GCA GCC TCT GGA TTC ACC TTC AAT ACC TAC GCC ATG AAC TGG GTC        96
Cys Ala Ala Ser Gly Phe Thr Phe Asn Thr Tyr Ala Met Asn Trp Val
                20                  25                  30

CGC CAG GCC CCA GGA AAG GGT TTG GAA TGG GTT GCT CGC ATA AGA AGT       144
Arg Gln Ala Pro Gly Lys Gly Leu Glu Trp Val Ala Arg Ile Arg Ser
            35                  40                  45

AAA AGT AAT AAT TAT GCA ACA TAT TAT GCC GAT TCA GTG AAA GAC AGG       192
Lys Ser Asn Asn Tyr Ala Thr Tyr Tyr Ala Asp Ser Val Lys Asp Arg
        50                  55                  60

TTC ACC ATC TCC AGA GAT GAT TCA CAA AGC ATG CTC TAT CTG CAA ATG       240
Phe Thr Ile Ser Arg Asp Asp Ser Gln Ser Met Leu Tyr Leu Gln Met
 65                  70                  75                  80

AAC AAC TTG AAA ACT GAG GAC ACA GCC ATG TAT TAC TGT GTG AGA CGG       288
Asn Asn Leu Lys Thr Glu Asp Thr Ala Met Tyr Tyr Cys Val Arg Arg
                 85                  90                  95

TTT GCT TAC TGG GCC CAA GGG ACT CTG GTC ACT GTC TCT GCA               330
Phe Ala Tyr Trp Ala Gln Gly Thr Leu Val Thr Val Ser Ala
                100                 105                 110
```

(2) INFORMATION FOR SEQ ID NO:24:

(i) SEQUENCE CHARACTERISTICS:
        (A) LENGTH: 110 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:24:

```
Glu Ser Gly Gly Gly Leu Val Gln Pro Lys Gly Ser Leu Lys Leu Ser
1               5                   10                  15

Cys Ala Ala Ser Gly Phe Thr Phe Asn Thr Tyr Ala Met Asn Trp Val
            20                  25                  30

Arg Gln Ala Pro Gly Lys Gly Leu Glu Trp Val Ala Arg Ile Arg Ser
        35                  40                  45

Lys Ser Asn Asn Tyr Ala Thr Tyr Tyr Ala Asp Ser Val Lys Asp Arg
    50                  55                  60

Phe Thr Ile Ser Arg Asp Asp Ser Gln Ser Met Leu Tyr Leu Gln Met
65                  70                  75                  80

Asn Asn Leu Lys Thr Glu Asp Thr Ala Met Tyr Tyr Cys Val Arg Arg
                85                  90                  95

Phe Ala Tyr Trp Ala Gln Gly Thr Leu Val Thr Val Ser Ala
            100                 105                 110
```

(2) INFORMATION FOR SEQ ID NO:25:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...357
        (D) OTHER INFORMATION:

(xi) SEQUENCE DESCRIPTION: SEQ ID NO:25:

```
GAA GTT AAG CTT GAG GAG TCT GGA GGA GGC TTG GTG CAA CCT GGA GGA       48
Glu Val Lys Leu Glu Glu Ser Gly Gly Gly Leu Val Gln Pro Gly Gly
1               5                   10                  15

TCC ATG AAA CTC TCC TGT GTT GCC TCT GGA TTC ACT TTC AGT AAC TAC       96
Ser Met Lys Leu Ser Cys Val Ala Ser Gly Phe Thr Phe Ser Asn Tyr
            20                  25                  30

TGG ATG AAC TGG GTC CGC CAG TCT CCA GAG AAG GGG CTT GAG TGG GTT      144
Trp Met Asn Trp Val Arg Gln Ser Pro Glu Lys Gly Leu Glu Trp Val
        35                  40                  45

GCT GAA GTT AGA TTG AAA TCT AAT TAT GCA ACA CAT TAT GCG GAG TCT      192
Ala Glu Val Arg Leu Lys Ser Asn Tyr Ala Thr His Tyr Ala Glu Ser
    50                  55                  60

GTG AAA GGG AGG TTC ACC ATC TCA AGA GAT GAT TCC AAA AGT AGT GTC      240
Val Lys Gly Arg Phe Thr Ile Ser Arg Asp Asp Ser Lys Ser Ser Val
65                  70                  75                  80

TAC CTG CAA ATG AAC AAC TTA AGA GCT GAA GAC ACT GGA ATT TAT TAC      288
Tyr Leu Gln Met Asn Asn Leu Arg Ala Glu Asp Thr Gly Ile Tyr Tyr
                85                  90                  95
```

```
TGT ACC CGT TAC GGT AGA GAG GGG GGG GTT GCT TAC TGG GGG CAA GGG        336
Cys Thr Arg Tyr Gly Arg Glu Gly Gly Val Ala Tyr Trp Gly Gln Gly
            100                 105                 110

ACT CTG GTC ACT GTC TCT GCA                                            357
Thr Leu Val Thr Val Ser Ala
        115
```

(2) INFORMATION FOR SEQ ID NO:26:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:26:

```
Glu Val Lys Leu Glu Glu Ser Gly Gly Gly Leu Val Gln Pro Gly Gly
 1               5                  10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Val Arg Leu Lys Ser Asn Tyr Ala Thr His Tyr Ala Glu Ser
    50                  55                  60

Val Lys Gly Arg Phe Thr Ile Ser Arg Asp Asp Ser Lys Ser Ser Val
65                  70                  75                  80

Tyr Leu Gln Met Asn Asn Leu Arg Ala Glu Asp Thr Gly Ile Tyr Tyr
                85                  90                  95

Cys Thr Arg Tyr Gly Arg Glu Gly Gly Val Ala Tyr Trp Gly Gln Gly
            100                 105                 110

Thr Leu Val Thr Val Ser Ala
        115
```

(2) INFORMATION FOR SEQ ID NO:27:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...360
        (D) OTHER INFORMATION:

(xi) SEQUENCE DESCRIPTION: SEQ ID NO:27:

```
GAA GTG AAG ACT GAG GAG TCT GGA GGA GGC TTG GTT CAA CCT GGA GGA        48
Glu Val Lys Thr Glu Glu Ser Gly Gly Gly Leu Val Gln Pro Gly Gly
  1               5                  10                  15

TCC ATG AAA CTC TCC TGT GTT GCC TCT GGA TTC ACT TTC AGT AAC TAC        96
Ser Met Lys Leu Ser Cys Val Ala Ser Gly Phe Thr Phe Ser Asn Tyr
                 20                  25                  30

TGG ATG AAC TGG GTC CGC CAG TCT CCA GAG AAG GGG CTT GAG TGG GTT       144
Trp Met Asn Trp Val Arg Gln Ser Pro Glu Lys Gly Leu Glu Trp Val
             35                  40                  45

GCT GAA ATT AGA TTG AAA TCT AAT AAT TAT GCA ACA CAT TAT GCG GAG       192
Ala Glu Ile Arg Leu Lys Ser Asn Asn Tyr Ala Thr His Tyr Ala Glu
 50                  55                  60

TCT GTG AAA GGG AGG TTC ACC ATC TCA AGA GAT GAT TCC AAA AGT AGT       240
Ser Val Lys Gly Arg Phe Thr Ile Ser Arg Asp Asp Ser Lys Ser Ser
 65                  70                  75                  80

GTC TAC CTG CAA ATG AAC AAC TTA AGA GCT GAA GAC ACT GGC ATT TAT       288
Val Tyr Leu Gln Met Asn Asn Leu Arg Ala Glu Asp Thr Gly Ile Tyr
                 85                  90                  95

TAC TGT ACC CGT TAC GGT AGA GAG GGG GGG TTT GCT TAC TGG GGG GAA       336
Tyr Cys Thr Arg Tyr Gly Arg Glu Gly Gly Phe Ala Tyr Trp Gly Glu
                100                 105                 110

GGG ACT CTG GTC ACT GTC TCT GCA                                       360
Gly Thr Leu Val Thr Val Ser Ala
            115                 120

(2) INFORMATION FOR SEQ ID NO:28:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:28:

Glu Val Lys Thr Glu Glu Ser Gly Gly Gly Leu Val Gln Pro Gly Gly
  1               5                  10                  15

Ser Met Lys Leu Ser Cys Val Ala Ser Gly Phe Thr Phe Ser Asn Tyr
                 20                  25                  30

Trp Met Asn Trp Val Arg Gln Ser Pro Glu Lys Gly Leu Glu Trp Val
             35                  40                  45

Ala Glu Ile Arg Leu Lys Ser Asn Asn Tyr Ala Thr His Tyr Ala Glu
 50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Ala Glu Asp Thr Gly Ile Tyr
                 85                  90                  95

Tyr Cys Thr Arg Tyr Gly Arg Glu Gly Gly Phe Ala Tyr Trp Gly Glu
                100                 105                 110

Gly Thr Leu Val Thr Val Ser Ala
            115                 120
```

(2) INFORMATION FOR SEQ ID NO:29:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...321
        (D) OTHER INFORMATION:

(xi) SEQUENCE DESCRIPTION: SEQ ID NO:29:

```
GAA ACA ACT GTG ACC CAG TCT CCA GCA TCC CTG TCC GTG GCT ACA GGA        48
Glu Thr Thr Val Thr Gln Ser Pro Ala Ser Leu Ser Val Ala Thr Gly
 1               5                  10                  15

GAA AAA GTC ACT ATC AGA TGC ATA ACC AGC ACT GAT ATT GAT GAT GAT        96
Glu Lys Val Thr Ile Arg Cys Ile Thr Ser Thr Asp Ile Asp Asp Asp
             20                  25                  30

ATG AAC TGG TAC CAG CAG AAG CCA GGG GAA CCT CCT AAG CTC CTT ATT       144
Met Asn Trp Tyr Gln Gln Lys Pro Gly Glu Pro Pro Lys Leu Leu Ile
         35                  40                  45

TCA GAA GGC AAT ACT CTT CGT CCT GGA GTC CCA TCC CGA TTC TCC AGC       192
Ser Glu Gly Asn Thr Leu Arg Pro Gly Val Pro Ser Arg Phe Ser Ser
     50                  55                  60

AGT GGC TAT GGC ACA GAT TTT GTT TTT ACA ATT GAA AAC ACG CTC TCA       240
Ser Gly Tyr Gly Thr Asp Phe Val Phe Thr Ile Glu Asn Thr Leu Ser
 65                  70                  75                  80

GAA GAT GTT GCA GAT TAC TAC TGT TTG CAA AGT GAT AAC ATG CCT CTC       288
Glu Asp Val Ala Asp Tyr Tyr Cys Leu Gln Ser Asp Asn Met Pro Leu
                 85                  90                  95

ACG TTC GGT GCT GGG ACC AAG CTG GAG CTG AAA                           321
Thr Phe Gly Ala Gly Thr Lys Leu Glu Leu Lys
             100                 105
```

(2) INFORMATION FOR SEQ ID NO:30:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:30:

```
Glu Thr Thr Val Thr Gln Ser Pro Ala Ser Leu Ser Val Ala Thr Gly
 1               5                  10                  15

Glu Lys Val Thr Ile Arg Cys Ile Thr Ser Thr Asp Ile Asp Asp Asp
             20                  25                  30
```

```
Met Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Thr Leu Ser
 65              70                  75                  80

Glu Asp Val Ala Asp Tyr Tyr Cys Leu Gln Ser Asp Asn Met Pro Leu
                85                  90                  95

Thr Phe Gly Ala Gly Thr Lys Leu Glu Leu Lys
            100                 105
```

(2) INFORMATION FOR SEQ ID NO:31:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...321
        (D) OTHER INFORMATION:

(xi) SEQUENCE DESCRIPTION: SEQ ID NO:31:

```
GAC ATT GTG ATG ACC CAG TCT CAA AAA TTC ATG TCC ACA TCA GTA GGA      48
Asp Ile Val Met Thr Gln Ser Gln Lys Phe Met Ser Thr Ser Val Gly
 1               5                  10                  15

GAC AGG GTC AGC GTC ACC TGC AAG GCC AGT CAG AAT GTG GGT ACT AAT      96
Asp Arg Val Ser Val Thr Cys Lys Ala Ser Gln Asn Val Gly Thr Asn
                20                  25                  30

GTA GCC TGG TAT CAA CAG AAA CCA GGG CAA TCT CCT AAA GCA CTG ATT     144
Val Ala Trp Tyr Gln Gln Lys Pro Gly Gln Ser Pro Lys Ala Leu Ile
            35                  40                  45

TAC TCG GCA TCC TAC CGG TAC AGT GGA GTC CCT GAT CGC TTC ACA GGC     192
Tyr Ser Ala Ser Tyr Arg Tyr Ser Gly Val Pro Asp Arg Phe Thr Gly
    50                  55                  60

AGT GGA TCT GGG ACA GAT TTC ACT CTC ACC ATC AGC GAT GTG CAG TCT     240
Ser Gly Ser Gly Thr Asp Phe Thr Leu Thr Ile Ser Asp Val Gln Ser
 65              70                  75                  80

GAA GAC TTG GCA GAG TAT TTC TGT CAG CAA TAT AAC ATC TAT CCG CTC     288
Glu Asp Leu Ala Glu Tyr Phe Cys Gln Gln Tyr Asn Ile Tyr Pro Leu
                85                  90                  95

ACG TTC GGT GCT GGG ACC AAG CTG GAG CTG AAA                         321
Thr Phe Gly Ala Gly Thr Lys Leu Glu Leu Lys
            100                 105
```

(2) INFORMATION FOR SEQ ID NO:32:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:32:

```
Asp Ile Val Met Thr Gln Ser Gln Lys Phe Met Ser Thr Ser Val Gly
 1               5                  10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
        50                  55                  60

Ser Gly Ser Gly Thr Asp Phe Thr Leu Thr Ile Ser Asp Val Gln Ser
65                  70                  75                  80

Glu Asp Leu Ala Glu Tyr Phe Cys Gln Gln Tyr Asn Ile Tyr Pro Leu
                85                  90                  95

Thr Phe Gly Ala Gly Thr Lys Leu Glu Leu Lys
            100                 105
```

(2) INFORMATION FOR SEQ ID NO:33:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...321
        (D) OTHER INFORMATION:

(xi) SEQUENCE DESCRIPTION: SEQ ID NO:33:

```
GAA ACA ACT GTG ACC CAG TCT CCA GCA TCC CTG TCC GTG GCT ACA GGA      48
Glu Thr Thr Val Thr Gln Ser Pro Ala Ser Leu Ser Val Ala Thr Gly
 1               5                  10                  15

GAA AAA GTC ACT ATC AGA TGC ATA ACC AGC ACT GAT ATT GAT GAT GAT      96
Glu Lys Val Thr Ile Arg Cys Ile Thr Ser Thr Asp Ile Asp Asp Asp
                20                  25                  30

ATG AAC TGG TAC CAG CAG AAG CCA GGG GAA CCT CCT AAG CTC CTT ATT     144
Met Asn Trp Tyr Gln Gln Lys Pro Gly Glu Pro Pro Lys Leu Leu Ile
            35                  40                  45

TCA GAA GGC AAT ACT CTT CGT CCT GGA GTC CCA TCC CGA TTC TCC AGC     192
Ser Glu Gly Asn Thr Leu Arg Pro Gly Val Pro Ser Arg Phe Ser Ser
        50                  55                  60

AGT GGC TAT GGC ACA GAT TTT GTT TTT ACA ATT GAA AAC ACG CTC TCA     240
Ser Gly Tyr Gly Thr Asp Phe Val Phe Thr Ile Glu Asn Thr Leu Ser
65                  70                  75                  80
```

```
GAA GAT GTT GCA GAT TAC TAC TGT TTG CAA AGT GAT AAC ATG CCA TTC         288
Glu Asp Val Ala Asp Tyr Tyr Cys Leu Gln Ser Asp Asn Met Pro Phe
                85                  90                  95

ACG TTC GGC TCG GGG ACA AAG TTG GAA ATA AAA                             321
Thr Phe Gly Ser Gly Thr Lys Leu Glu Ile Lys
            100                 105
```

(2) INFORMATION FOR SEQ ID NO:34:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:34:

```
Glu Thr Thr Val Thr Gln Ser Pro Ala Ser Leu Ser Val Ala Thr Gly
 1               5                  10                  15

Glu Lys Val Thr Ile Arg Cys Ile Thr Ser Thr Asp Ile Asp Asp Asp
                20                  25                  30

Met Asn Trp Tyr Gln Gln Lys Pro Gly Glu Pro Pro Lys Leu Leu Ile
            35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Thr Leu Ser
65                  70                  75                  80

Glu Asp Val Ala Asp Tyr Tyr Cys Leu Gln Ser Asp Asn Met Pro Phe
                85                  90                  95

Thr Phe Gly Ser Gly Thr Lys Leu Glu Ile Lys
            100                 105
```

(2) INFORMATION FOR SEQ ID NO:35:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...345
        (D) OTHER INFORMATION:

(xi) SEQUENCE DESCRIPTION: SEQ ID NO:35:

```
GAG GTG CAG CTT GTT GAG TCT GGT GGA GGA TTG GTG CAG CCT AAA GGG          48
Glu Val Gln Leu Val Glu Ser Gly Gly Gly Leu Val Gln Pro Lys Gly
 1               5                  10                  15
```

```
TCA TTG AAA CTC TCA TGT GCA GCC TCT GGA TTC ACC TTC AAT ACC TAC      96
Ser Leu Lys Leu Ser Cys Ala Ala Ser Gly Phe Thr Phe Asn Thr Tyr
            20                  25                  30

GCC ATG AAC TGG GTC CGC CAG CTC CAA GGA AAG GGT TTG GAA TGG GTT     144
Ala Met Asn Trp Val Arg Gln Leu Gln Gly Lys Gly Leu Glu Trp Val
        35                  40                  45

GCT CGC ATA AGA AGT AAA AGT AAT AAT TAT GCA ACA TAT TAT GCC GAT     192
Ala Arg Ile Arg Ser Lys Ser Asn Asn Tyr Ala Thr Tyr Tyr Ala Asp
    50                  55                  60

TCA GTG AAA GAC AGG TTC ACC ATC TCC AGA GAT GAT TCA CAA AGC ATG     240
Ser Val Lys Asp Arg Phe Thr Ile Ser Arg Asp Asp Ser Gln Ser Met
65                  70                  75                  80

CTC TAT CTG CAA ATG AAC AAC TTG AAA ACT GAG GAC ACA GCC ATG TAT     288
Leu Tyr Leu Gln Met Asn Asn Leu Lys Thr Glu Asp Thr Ala Met Tyr
                85                  90                  95

TAC TGT GTG AGA CGG AGG GAC TAC TGG GGT CAA GGA ACC TCA GTC ACC     336
Tyr Cys Val Arg Arg Arg Asp Tyr Trp Gly Gln Gly Thr Ser Val Thr
            100                 105                 110

GTC TCC TCA                                                         345
Val Ser Ser
        115
```

(2) INFORMATION FOR SEQ ID NO:36:

(i) SEQUENCE CHARACTERISTICS:
        (A) LENGTH: 115 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:36:

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Leu Gln Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Arg Arg Asp Tyr Trp Gly Gln Gly Thr Ser Val Thr
            100                 105                 110

Val Ser Ser
        115
```

(2) INFORMATION FOR SEQ ID NO:37:

(i) SEQUENCE CHARACTERISTICS:
        (A) LENGTH: 372 base pairs (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...372
        (D) OTHER INFORMATION:

(xi) SEQUENCE DESCRIPTION: SEQ ID NO:37:

```
GAG GTG AAG CTG GTG GAG TCT GGA GGA GGC TTG GTA CAG CCT GGG GGT        48
Glu Val Lys Leu Val Glu Ser Gly Gly Gly Leu Val Gln Pro Gly Gly
 1               5                  10                  15

TCT CTG AGA CTC TCC TGT GCA ACT TCT GGG TTC ACC TTC ACT GAT TAC        96
Ser Leu Arg Leu Ser Cys Ala Thr Ser Gly Phe Thr Phe Thr Asp Tyr
            20                  25                  30

TAC ATG AGC TGG GTC CGC CAG CCT CCA GGA AAG GCA CTT GAG TGG TTG       144
Tyr Met Ser Trp Val Arg Gln Pro Pro Gly Lys Ala Leu Glu Trp Leu
        35                  40                  45

GGT TTG ATT AGA AAC AAA GCT AAT GGT TAC ACA ACA GAG TAC AGT GCA       192
Gly Leu Ile Arg Asn Lys Ala Asn Gly Tyr Thr Thr Glu Tyr Ser Ala
    50                  55                  60

TCT GTG AAG GGT CGG TTC ACC ATC TCC AGA GAT AAT TCC CAA AGC ATC       240
Ser Val Lys Gly Arg Phe Thr Ile Ser Arg Asp Asn Ser Gln Ser Ile
65                  70                  75                  80

CTC TAT CTT CAA ATG AAC ACC CTG AGA GCT GAG GAC AGT GCC ACT TAT       288
Leu Tyr Leu Gln Met Asn Thr Leu Arg Ala Glu Asp Ser Ala Thr Tyr
                85                  90                  95

TAC TGT GCA AGA GAT ATC TAC TAT GAT TAC GAC TAC TAT GCT ATG GAC       336
Tyr Cys Ala Arg Asp Ile Tyr Tyr Asp Tyr Asp Tyr Tyr Ala Met Asp
            100                 105                 110

TAC TGG GGT CAA GGA ACC TCA GTC ACC GTC TCC TCA                       372
Tyr Trp Gly Gln Gly Thr Ser Val Thr Val Ser Ser
        115                 120
```

(2) INFORMATION FOR SEQ ID NO:38:

(i) SEQUENCE CHARACTERISTICS:
        (A) LENGTH: 124 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:38:

```
Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
            20                  25                  30
```

```
Tyr Met Ser Trp Val Arg Gln Pro Pro Gly Lys Ala Leu Glu Trp Leu
        35                  40                  45

Gly Leu Ile Arg Asn Lys Ala Asn Gly Tyr Thr Thr Glu Tyr Ser Ala
 50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Ala Glu Asp Ser Ala Thr Tyr
                 85                  90                  95

Tyr Cys Ala Arg Asp Ile Tyr Tyr Asp Tyr Asp Tyr Tyr Ala Met Asp
                100                 105                 110

Tyr Trp Gly Gln Gly Thr Ser Val Thr Val Ser Ser
        115                 120
```

(2) INFORMATION FOR SEQ ID NO:39:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...111
        (D) OTHER INFORMATION:

(xi) SEQUENCE DESCRIPTION: SEQ ID NO:39:

```
CAC TGG AAC CAA CAG AAA CCA GGA CAG CCA CCC AGA CTC CTC ATC TAT        48
His Trp Asn Gln Gln Lys Pro Gly Gln Pro Pro Arg Leu Leu Ile Tyr
 1               5                  10                  15

CTT GTA TCC AAC CTA GAA TCT GGG GTC CCT GCC AGG TTC AGT GGC AGT        96
Leu Val Ser Asn Leu Glu Ser Gly Val Pro Ala Arg Phe Ser Gly Ser
             20                  25                  30

GGG TCT GGG ACA GAC                                                    111
Gly Ser Gly Thr Asp
         35
```

(2) INFORMATION FOR SEQ ID NO:40:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:40:

His Trp Asn Gln Gln Lys Pro Gly Gln Pro Pro Arg Leu Leu Ile Tyr

```
  1               5                   10                  15
Leu Val Ser Asn Leu Glu Ser Gly Val Pro Ala Arg Phe Ser Gly Ser
            20                  25                  30

Gly Ser Gly Thr Asp
        35
```

(2) INFORMATION FOR SEQ ID NO:41:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:41:

```
GAAGATCTAG ACTTACTATG CAGCATCAGC                                    30
```

(2) INFORMATION FOR SEQ ID NO:42:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:42:

```
AGGAGACTAG TGGTTACTAA TTTGGGAAGG ACTG                               34
```

(2) INFORMATION FOR SEQ ID NO:43:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:43:

```
GAGACGACTA GTGGTGGCGG TGGCTCTCCA TTCGTTTGTG AATATCAA                48
```

(2) INFORMATION FOR SEQ ID NO:44:

-continued

```
    (i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:44:

TTACTAGCTA GCATAATAAC GGAATACCCA AAAGAACTGG                              40

(2) INFORMATION FOR SEQ ID NO:45:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:45:

TATGCTAGCT AGTAACACGA CAGGTTTCCC GACTGG                                  36

(2) INFORMATION FOR SEQ ID NO:46:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:46:

AGCTTTGAAT TCGTGAAATT GTTATCCGCT                                         30
```

LEAD BINDING POLYPEPTIDES AND NUCLEOTIDES CODING THEREFORE

This application is a continuation in part of PCT/US96/09258, filed Jun. 5, 1996 which is a continuation in part of U.S. Ser. No. 08/541,373, filed Oct. 10, 1995 (abandoned), which is a continuation in part of U.S. Ser. No. 08/462,798, filed Jun. 5, 1995 (abandoned).

BACKGROUND OF THE INVENTION

Small chemical moieties, such as heavy metal ions, can and often do affect the environment and biological systems. These effects become astounding when it is realized that minute quantities of these small moieties are involved. Moreover, the presence or absence of low concentrations of small moieties in the environment can have long term consequences. Minute quantities of metallic cations, such as lead cations, can regulate, influence, change or toxify the environment or biological systems.

The detection, removal, addition or neutralization of such minute quantities constitutes a focal point for continued research in many fields. For example, many efforts have been made to detect and remove minute, toxic amounts of heavy metal ions such as lead or mercury from the environment. The efforts often have not been successful or economical for widespread application. On the other hand, minute concentrations of other heavy metals are important for the proper function of biological organisms. Zinc, for example, plays a major role in wound healing.

Heavy metal can exhibit dual roles. For example, lead is used in glass making and in chemical manufacturing operations. Yet when ingested by mammals, such as from drinking water, lead may be highly toxic in very small amounts. Hence, detection and quantification of minute concentrations of a heavy metal, such as lead, in drinking water and other media would serve exploratory, safety and regulatory goals.

It would, therefore, be highly desirable to identify and control minute quantities of heavy metals, e.g., lead cations, in aqueous biological or inanimate systems. In most contexts, however, the detection, removal, addition or neutralization of heavy metals, is a difficult and expensive and often unfeasible if not impossible task. Other metallic contaminants often mimic the heavy metal of interest and result in measurement interference. Moreover, the detection methods employed today are usually not sufficiently sensitive at the minute quantities under consideration. Consequently, it is desirable to develop reliable and economic methods for accurately identifying and controlling minute quantities of a particular heavy metal in the presence of other heavy metals.

Antibodies would seem to be uniquely suited for this task. Their high degree of specificity for a known antigen would avoid the potential interference caused by contaminants. The sensitivity of antibodies in assays to detect analytes in the picomolar or lower range would permit accurate and efficient targeting and detection at minute levels.

Monoclonal antibodies, of course, come to mind as especially suited agents for practice of this technique. Since Kohler and Milstein published their article on the use of somatic cell hybridization to produce monoclonal antibodies (*Nature* 256:495 (1974)), immunologists have developed many monoclonal antibodies which strongly and specifically immunoreact with antigens.

Notwithstanding this suggestion, the conventional understanding about immunology teaches that antibodies against small moieties, such as heavy metals, cannot be developed. The mammal immunization step, which is key for the production of monoclonal antibodies, typically requires a molecule that is large enough to cause antigenic reaction. Medium sized molecules (haptens), which are not of themselves immunogenic, can induce immune reaction by binding to an immunogenic carrier. Nevertheless, immunologists view small moieties such as metallic cations, as not large or structurally complex enough to elicit an antibody response. The molecular size and lack of complexity of an inorganic cation is thought to render it insufficient for eliciting an antibody response.

Several immunologists have reported production of monoclonal antibodies to metallic ion chelates. For example, in U.S. Pat. No. 4,722,892, monoclonal antibodies are disclosed which immunoreact with a complex of a chelating agent, such as ethylene diamine tetracetate (EDTA), and a heavy metal such as indium. In EPO Patent Application 0235457, monoclonal antibodies that immunoreact with cyanide complexes of gold and/or silver are disclosed. In these instances, however, the monoclonal antibodies bind with the metal chelate complex rather than the bare metallic ion itself. Disadvantages of antigen measurement methods based on such antibodies include: the complicated reagents involved in detection, lack of simple tests that discriminate among antigens, cross-reactivity with chelates of other antigens and cross-reactivity with the chelating agent itself.

Other instances of monoclonal antibody combinations with metals involve metal tags. The metals or metal chelates are bound to the antibody at a site remote from the antigen binding site or sites. The metal tag is not the antigen. Instead, the metal tag is used to indicate the presence of the monoclonal antibody when it reacts with its specific antigen. See for example, V.P. Torchilian et al., *Hybridoma*, 6, 229 (1987); and C.F. Meares, *Nuclear Medical Biology*, 13, 311–318 (1986).

Accordingly, there exists a need to develop polypeptides that immunoreact with heavy metals per se and with lead ions in particular. This would permit the development of methods for detecting or neutralizing heavy metals within, adding heavy metals to, or removing heavy metals from biological or inanimate systems through the use of the monoclonal antibodies. There also exists a need for the development of nucleic acid sequences coding for polypeptides which selectively bind with lead cations and the development of methods of expressing and translating these nucleic acid sequences to produce metal binding polypeptides.

SUMMARY OF THE INVENTION

The present invention provides a metal binding polypeptide which selectively binds a heavy metal, such as a lead cation. The metal binding polypeptide includes an amino acid sequence for a variable region from a monoclonal antibody, wherein the monoclonal antibody immunoreacts with a lead cation. For example, the metal binding polypeptide may include an amino acid sequence for a heavy chain Fd fragment (consisting of the heavy-chain variable region and heavy-chain constant region 1 domains) from the monoclonal antibody. The metal binding polypeptide may further include a heavy chain Fc fragment fused to the heavy chain Fd fragment or a phage coat protein or portion thereof fused to the heavy chain Fd fragment. Alternatively, the metal binding polypeptide may include an amino acid sequence for a light chain from the monoclonal antibody.

Another embodiment of the invention provides a recombinantly produced Fab fragment that immunoreacts with a lead cation. The recombinantly produced lab fragment includes an amino acid sequence for a variable region from a monoclonal antibody which immunoreacts with the lead cation. Preferably, the Fab fragment includes a heavy chain Fd fragment or a light chain from the monoclonal antibody.

The present invention also provides a purified antibody which includes a Fab fragment. The Fab fragment immunoreacts with a lead cation and includes an amino acid sequence selected from a group of sequences for a variable region of certain specified monoclonal antibodies. The Fab fragment heavy chain preferably includes an amino acid sequence selected from a group of the sequences for the heavy chain variable region of the specified monoclonal antibodies. In another preferred embodiment, the Fab fragment light chain includes an amino acid sequence selected from a group of the sequences for the light chain variable region of the specified monoclonal antibodies. The monoclonal antibody may be a recombinantly produced monoclonal antibody.

The invention is also directed to a heavy chain of the monoclonal antibody. The heavy chain preferably includes a sequence selected from a group of the sequences for the heavy chain variable region of certain specified monoclonal antibodies. The invention is also directed to a light chain of the monoclonal antibody. As with the heavy chain, the light chain preferably includes a sequence selected from a group of the sequences for the light chain variable region of certain specified monoclonal antibodies.

Yet another embodiment of the invention is directed to an isolated nucleic acid sequence coding for a variable region of a monoclonal antibody, e.g., the heavy chain variable region or the light chain variable region of the monoclonal antibody. The monoclonal antibody immunoreacts with a lead cation. Alternatively, the isolated nucleic acid sequence may code for the heavy chain Fd fragment, the entire heavy chain or the entire light chain of the monoclonal antibody.

The present invention is also directed to an expression cassette. The expression cassette includes a nucleic acid sequence coding for a variable region of the monoclonal antibody which immunoreacts with a lead cation. The nucleic acid sequence coding for the variable region is operably linked to a promoter functional in a vector. The expression cassette may include the promoter operably linked to a nucleic acid sequence coding for a heavy chain Fd fragment of the monoclonal antibody. Alternatively, the expression cassette may include the promoter operably linked to a nucleic acid sequence coding for a light chain of the monoclonal antibody. The expression cassette may also include a leader sequence located between the promoter and the nucleic acid sequence coding for the monoclonal antibody chain. The leader sequence may function to direct the heavy or light chain to a membrane in a host cell or to cause the antibody chain to be secreted by the host cell.

In another embodiment, the present invention provides a fusion protein which includes a phage coat protein or portion thereof fused to an amino acid sequence for a heavy chain variable region from the monoclonal antibody. The fusion protein preferably includes the heavy chain Fd fragment of the monoclonal antibody. The fusion protein may be present as part of the coat of a phage and, preferably, the coat of a filamentous phage.

Another embodiment of the present invention is directed to an expression cassette coding for a fusion protein. This expression cassette includes a first nucleic acid sequence coding for a heavy chain Fd fragment of a monoclonal antibody which reacts with a lead cation. The first nucleic acid sequence is linked for co-expression to a second nucleic acid sequence, such as a nucleic acid sequence coding for a phage coat protein or a portion thereof, to form a nucleic acid sequence encoding the fusion protein. The fusion protein includes the heavy chain Fd fragment fused to the phage coat protein or portion thereof. The expression cassette coding for the fusion protein also includes a promoter that is functional in a vector. The promoter is operably linked to the first and second DNA sequences and provides for expression of the fusion protein. The expression cassette may also include a leader sequence which directs expression of the fusion protein to a membrane of a host cell. The leader sequence is located between the promoter and the nucleic acid sequence coding for the fusion protein. In addition, the expression cassette may include a third nucleic acid sequence coding for a peptide linker. The third nucleic acid sequence is typically located between the first and second nucleic acid sequences. The expression cassette may optionally include a fourth nucleic acid sequence coding for a light chain of a monoclonal antibody. Preferably, the light chain is a light chain of a monoclonal antibody that immunoreacts with a lead cation. The present invention also provides a phagemid vector which includes one of the expression cassettes described above.

The invention is also directed to methods for detecting, removing, adding, or neutralizing the heavy metals in biological and inanimate systems through the use of the metal binding polypeptides, heavy and light chains, fusion proteins, recombinantly produced Fab fragments and monoclonal antibodies described above.

The advantages of the invention include among others: the lack of complication by additional reagents, a high discrimination against similar metallic cations, lack of cross-reactivity with similar metallic cations, and lack of cross-reactivity with test reagents.

The metal binding polypeptide of the invention binds with a heavy metal per se, and preferably with a lead cation per se. The metal binding polypeptide binds with a heavy metal cation which is at least partially exposed, i.e., a heavy metal cation which is not complexed or enveloped. For example, the heavy metal cation may be associated with a spacer arm which includes a sulfur atom as a Lewis base group. The state of the heavy metal during the immunoreaction is preferably one of non-coordination with any other substance; in other words, bare or exposed.

Preferably, the metal binding polypeptide exhibits a substantially high degree of specific immunoreactivity toward the heavy metal. More preferably, the metal binding polypeptide includes a portion of a recombinantly produced Fab fragment (e.g., the light chain or the heavy chain Fd fragment of the Fab fragment) and has an association constant for a heavy metal such as a lead cation that is about 10,000 fold greater than the association constant for the immunogen compound without the heavy metal. Also preferably, the metal binding polypeptide is immunospecific for a particular member of a group of very similar heavy metals. The monoclonal antibody will typically exhibit a relative association constant for such a particular heavy metal that is about 10,000 fold greater than that for the other heavy metals of such a group.

The hybridoma of the invention, which produces the monoclonal antibody, is formed from immune cells that are specific for the heavy metal. The formation may be accomplished by fusion of an immortal mammal cell line and mammalian immune cells from a second mammal previously immunized with an immunogen compound which contains the heavy metal. A lead cation monoclonal antibody produced by this first type of hybridoma is hereinafter referred to as a "Group 1 lead cation monoclonal antibody." Alternatively, the hybridoma may be formed by fusion of an immortal mammal cell line and mammalian immune cells from a second mammal previously immunized with a second monoclonal antibody capable of immunoreacting with the heavy metal. A lead cation monoclonal antibody produced by this latter type of hybridoma is hereinafter referred to as a "Group 3 lead cation monoclonal antibody." Selection of the appropriate hybridoma may be carried out by cross-screening the secreted monoclonal antibody against the heavy metal and against controls.

The immunogen compound of the invention is typically composed of a biopolymer carrier, a spacer arm covalently bonded to the carrier and the heavy metal coordinated to the spacer arm. The spacer arm is preferably semi-rigid and has at least one heavy metal coordination site. This arrangement maintains the heavy metal in at least a partially exposed state and prevents substantially complete inclusion or chelation of the heavy metal by spacer arm and/or carrier. The biopolymer carrier may be a polysaccharide, a synthetic polyamide or preferably a protein. Preferred classes include blood or tissue sera proteins.

The spacer arm is generally no more than about 25 atoms in length. Preferably, the spacer arm is composed of one of three classes: an oligopeptide, an aliphatic compound or an aliphatic fragment. More preferably, the spacer arm is an oligopeptide. The first two classes are generally each substituted with no more than about 2 pendent Lewis acid or base groups, and a coupling group for forming a covalent bond with the protein carrier. The aliphatic fragment is substituted by a coupling group for forming a covalent bond with the protein carrier, and a carboxylic acid, hydroxyl, mercapto, amine or other group adapted for interacting with the heavy metal. For each class of spacer arm, the coupling group is an amine, carboxylic acid, aldehyde, hydroxyl or mercapto group.

A preferred spacer arm for metallic cations is an oligopeptide or aliphatic compound having no more than about 2 pendent Lewis base groups wherein the deformation of the electron shell of the Lewis base group is approximately of the same character as the deformation of the electron shell of the metallic cation. Especially preferred Lewis base groups for transition elements and the heavy metals are those containing sulfur, such as a sulfonate or thiol group. Especially preferred are spacer arms which include glutathione and cysteine, mercapto ethanol amine, dithiothreitol, amines and peptides containing sulfur, and the like. Other preferred spacer arms include a carboxylic acid group or a phosphorus-containing Lewis base group such as a phosphonate anion.

The metallic cations are derived from metals such as period four transition metals, and period five, six and seven metals, transition elements and inner transition elements. The metallic cations of special mention as the heavy metal include those derived from zinc, lead, cadmium, bismuth, cobalt, arsenic, chromium, copper, nickel, strontium and mercury. Preferably, the metallic cations are lead cations, e.g., lead(II) cations.

The present invention also provides a method of forming a hybridoma which produces an antibody capable of immunoreacting with a lead cation and preferably with an exposed form of the lead cation. The method includes inoculating a mammal with a solution containing second antibodies which are capable of immunoreacting with the lead cation. Immune cells are isolated from the mammal and fused with an immortal mammal cell line from a second mammal. The resulting fused cell lines are selected for hybridomas which produce monoclonal antibodies capable of immunoreacting with a lead cation (Group 3 lead cation monoclonal antibodies; "Group 3 Pb mAbs").

Methods according to the invention utilize the metal binding polypeptide for detection, removal, neutralization or addition of the heavy metal respectively in, from, within or to a solid, liquid or gaseous medium. These methods utilize features such as metal binding polypeptide immobilization, heavy metal immobilization, competitive binding, and means employing an oscillating probe, a micromagnetic probe and other physiochemical methods typically used to monitor antigen-antibody interactions.

Methods for detection that are based upon heavy metal immobilization may indicate the presence of the heavy metal-metal binding polypeptide conjugate (e.g., a lead cation-Fab fragment conjugate) by known immunologic assay techniques. In a first step, the heavy metal may be coordinated with an immobilized spacer arm. The spacer arm can be any of the foregoing that will hold the heavy metal in at least a partially exposed state. It need not be the same spacer arm of the immunogen compound used to develop the metal binding polypeptide. Non-immobilized materials are then removed from the mixture holding the immobilized spacer arm-heavy metal. Addition of the metal binding polypeptide (e.g., Fab fragment), removal of uncomplexed metal binding polypeptide and immunoassay complete the steps for this detection method.

Methods for detection that are based upon an immobilized metal binding polypeptide may utilize a radioactive version of the heavy metal or a similar tagged form thereof. Such tags include fluorescent, colorimetric and other spectrally active groups that can be coordinated or bonded to the heavy metal like the spacer arm. A preferred tag is a spacer arm containing a spectrally active group. First, the immobilized monoclonal antibody is saturated with the tagged heavy metal. After removal of the non-immobilized components, an aliquot of the unknown heavy metal is added. It displaces a portion of the bound, tagged heavy metal and measurement of that amount displaced will determine the concentration of unknown metal.

Methods for detection that are based upon an oscillating probe utilize either an immobilized spacer arm for the heavy metal or preferably immobilized metal binding polypeptide. This method measures the change in frequency of an oscillating surface as a function of the change in weight of that surface due to the binding of the non-immobilized heavy metal or metal binding polypeptides are immobilized on the surface of a high frequency oscillating probe. The probe is placed into a medium containing an unknown quantity of heavy metal. Binding of the heavy metal to the immobilized metal binding polypeptide will change the oscillation frequency of the probe. Hence, the degree of change will indicate the level of heavy metal present.

When the heavy metal is present as a metal cation in an aqueous medium, an especially preferred method for detection utilizes an oligopeptide having reactive group(s) capable of coordinating with the metal cation. The oligopeptide and the metal binding polypeptide specific for the metal cation unknown are added to the aqueous medium. The medium then is assayed for the presence of metal binding polypeptide cation conjugate. The interaction of the metal binding polypeptide with the metal cation is independent of the order of addition of the reactants and is independent of the identity of the oligopeptide.

In an especially preferred version of this method, a fixed support is utilized. Here, either the oligopeptide or the metal binding polypeptide is immobilized on the fixed support. The method is then conducted as related above.

The invention, in addition, contemplates methods for heavy metal removal from, heavy metal neutralization within or heavy metal addition to biological or inanimate systems. For all methods, an effective amount of the metal binding polypeptide is combined in some fashion with at least part of the system. Pursuant to the removal method, metal binding polypeptide-heavy metal conjugate is removed by separation means such as immunoprecipitation, immobilization, chromatography, filtration and the like. Pursuant to the neutralization method, the metal binding polypeptide-heavy metal conjugate remains in the system until it is removed by non-specific means. Pursuant to the addition method, the metal binding polypeptide-heavy metal conjugate also remains in the system and the heavy metal is actively incorporated or otherwise used therein.

When the system participating in the foregoing methods is biological, the metal binding polypeptide may be combined with a pharmaceutically acceptable carrier. Preferably, the metal binding polypeptide will not of itself cause an undesirable immune response of the biological system. The biological systems contemplated according to the invention include unicellular organisms, multicellular simple organisms, cellular component systems, tissue cultures, plants and animals, including mammals.

The present invention also contemplates methods for removing heavy metallic cations or radioactive compounds from human fluids such as blood, serum or lymph by utilization of immobilized metal binding polypeptides. An extracorporeal shunt placed in the patient permits removal of the body fluid and its reintroduction. Passing the body fluid extracorporeally through a bed of immobilized metal binding polypeptide accomplishes the desired removal.

The present invention also contemplates a kit for assaying the presence and quantity of heavy metal in a biological or inanimate system. The kit includes aliquots of metal binding polypeptides in the appropriate buffer, as well as a fixed support for absorption of the heavy metal, washing solutions, reagents such as enzyme substrates, and metal binding polypeptide specific antisera conjugated to a detectable substrate.

BRIEF DESCRIPTION OF THE DRAWINGS

FIGS. 1A–1B depict the nucleotide sequences (corresponding to amino acids 1 through 113) for the heavy chain variable regions of the following monoclonal antibodies which immunoreact with a lead cation: 6B11 (SEQ. ID NO:1); 1254 (SEQ. ID NO:3); 8E7 (SEQ. ID NO:5); 10G1 (SEQ. ID NO:7); and 14F11 (SEQ. ID NO:9); and the deduced amino acid sequences: 6B11 (SEQ. ID NO:2); 1254 (SEQ. ID NO:4); 8E7 (SEQ. ID NO:6); 10G5 (SEQ. ID NO:8); and 14F11 (SEQ. ID NO:10). The numbering scheme is according to Kabat et al., Sequences of Proteins of Immunological Interest, vol. II. 5th edition, U.S. Department of Health and Human Services (1991) (hereinafter "Kabat"). Dashes indicate sequence identity with the 6B11 sequence; periods indicate gaps compared to the 1254 sequence.

FIG. 2 depicts the nucleotide sequences (corresponding to amino acids 5 through 108) of the light chain variable regions of the following monoclonal antibodies which immunoreact with a lead cation: 6B11 (SEQ. ID NO:11); 1254 (SEQ. ID NO:13); and 14F11 (SEQ. ID NO:15); and the deduced amino acid sequences: 6B11 (SEQ. ID NO:12); 1254 (SEQ. ID NO:14); and 14F11 (SEQ. ID NO:16). The numbering scheme is according to Kabat. Dashes indicate sequence identity with the 6B11 sequence.

FIGS. 3A–3B depict the nucleotide sequences (corresponding to amino acids 1 through 113) of the heavy chain variable regions of the following monoclonal antibodies which immunoreact with a lead cation: 13D10 (SEQ. ID NO:17); 11D11 (SEQ. ID NO:19); 14G11 (SEQ. ID NO:21); 6F5 (SEQ. ID NO:23); 7D10 (SEQ. ID NO:25); and 4E8 (SEQ. ID NO:27); and the deduced amino acid sequences 13D10 (SEQ. ID NO:18); 11D11 (SEQ. ID NO:20); 14G11 (SEQ. ID NO:22); 6F5 (SEQ. ID NO:24); 7D10 (SEQ. ID NO:26); and 4E8 (SEQ. ID NO:28). The numbering scheme is according to Kabat. Periods indicate gaps.

FIG. 4 depicts the nucleotide sequences (corresponding to amino acids 1 through 107) of the light chain variable regions of the monoclonal antibodies which immunoreact with a lead cation: 10G5 (SEQ. ID NO:29); 2E7 (SEQ. ID NO:31); 7D10 (SEQ. ID NO:33); and 6F5 (SEQ. ID NO:39); and the deduced amino acid sequences: 10G5 (SEQ. ID NO:30); 2E7 (SEQ. ID NO:32); 7D10 (SEQ. ID NO:34); and 6F5 (SEQ. ID NO:40). The numbering scheme is according to Kabat.

FIG. 5 depicts the nucleotide (SEQ. ID NO:35) and deduced amino acid sequences (SEQ. ID NO:36) for amino acids 1 through 113 of the heavy chain variable regions of monoclonal antibody 2B4 which immunoreacts with a lead cation. The numbering scheme is according to Kabat.

FIG. 6 depicts the nucleotide (SEQ. ID NO:37) and deduced amino acid sequences (SEQ. ID NO:38) for amino acids 1 through 113 of the heavy chain variable regions of monoclonal antibody 2E7 which immunoreacts with a lead cation. The numbering scheme is according to Kabat.

FIG. 7 shows the sensitivity of a set of Group 1 monoclonal antibodies (standardized to 50 $\mu$g/mL in PBS) to lead (as $Pb(NO_3)_2$). The indicated amounts of lead were added to a microtiter plate coated with an amino acid polymer formed from glutamic acid, lysine, and tyrosine (hereinafter "EKY polymer") and analyzed by ELISA. The measured absorbances were corrected for the absorbance of an average of four control wells.

FIG. 9 shows the sensitivity of a set Group 3 monoclonal antibodies (standardized to 50 $\mu$g/mL in PBS) to lead (as $Pb(NO_3)_2$). The indicated amounts of lead were added to a microtiter plate coated with EKY polymer and analyzed by ELISA. The measured absorbances were corrected for the absorbance of an average of four control wells.

FIG. 10 shows the sensitivity of a second set of Group 3 monoclonal antibodies (standardized to 50 $\mu$g/mL in PBS) to lead (as $Pb(NO_3)_2$). The indicated amounts of lead were added to a microtiter plate coated with EKY polymer and analyzed by ELISA. The measured absorbances were corrected for the absorbance of an average of four control wells.

FIG. 11 shows the sensitivity of a third set of Group 3 lead cation monoclonal antibodies (standardized to 50 $\mu$g/mL in PBS) to lead (as $Pb(NO_3)_2$) a Monoclonal antibody 3A6, which is specific for the PR8 influenza virus, was included as a control. The indicated amounts of lead were added to a microtiter plate coated with EKY polymer and analyzed by ELISA. The measured absorbances were corrected for the absorbance of an average of four control wells.

DETAILED DESCRIPTION OF THE INVENTION

Figure 8:
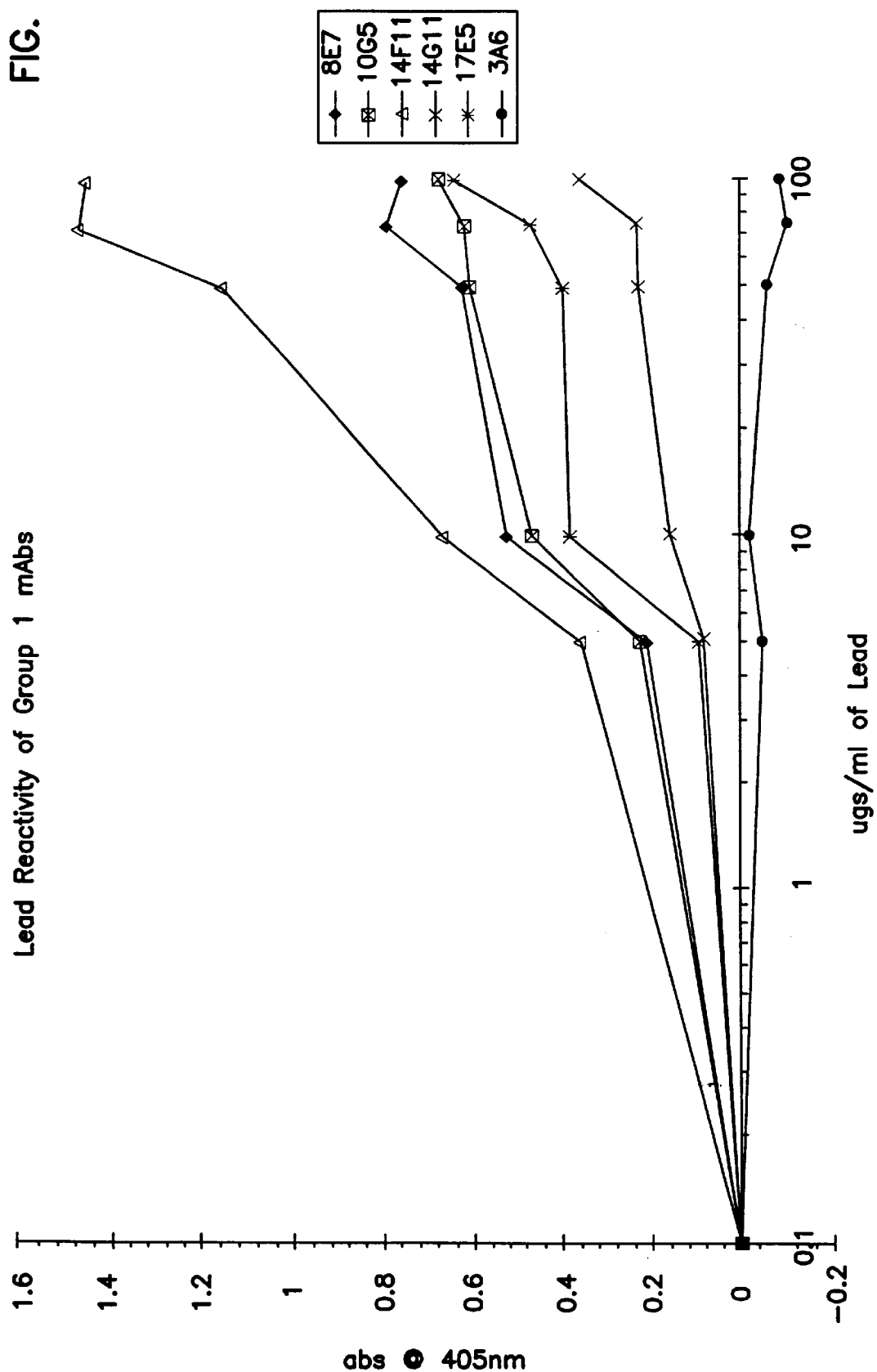
FIG. 8 shows the sensitivity of a second set of Group 1 monoclonal antibodies (standardized to 50 $\mu$g/mL in PBS) to lead (as $Pb(NO_3)_2$). The indicated amounts of lead were added to a microtiter plate coated with EKY polymer and analyzed by ELISA. The measured absorbances were corrected for the absorbance of an average of four control wells.

Metal binding polypeptides of the present invention are key to the development of methods for detecting, adding, neutralizing or removing minute quantities of heavy metals. Until the present invention, it was not possible to produce metal binding polypeptides which selectively bind with exposed heavy metal cations per se. The novel techniques for incorporating heavy metals into immunogen compounds and for administering these immunogen compounds to immune cell hosts allow production of the desired, immunospecific monoclonal antibodies according to the invention. These methods are believed to constitute an advancement in the understanding of immunology.

Although not intended as a limitation of the invention, it is now believed that mammalian immunogenic reactivity can be elicited by heavy metals. While they are smaller than the commonly recognized epitope size of approximately 20–25 angstroms, the heavy metals nevertheless can bind.

Notwithstanding these beliefs, the invention contemplates metal binding polypeptides which selectively bind with a heavy metal, e.g. monoclonal antibodies to heavy metals. Hybridomas for the monoclonal antibodies and immunogen compounds for carrying the heavy metals and inducing immunogenicity are also included in the present invention. The metal binding polypeptides may include a monoclonal antibody, a recombinantly produced Fab fragment or a fusion protein. The fusion protein includes the heavy chain variable region of a monoclonal antibody which is capable of immunoreacting with a heavy metal, such as a lead cation. The invention also provides methods for the detection, addition, neutralization or removal of heavy metals using the metal binding polypeptides.

Monoclonal Antibodies

The monoclonal antibodies of the invention are mammalian immunoglobulin proteins which have strong affinity constants for a specific heavy metal. Preferably, the monoclonal antibodies are from the IgG, IgA, IgM and IgE classes of antibodies, and more preferably, from the IgA, and IgM classes of antibodies. The heavy metal monoclonal antibodies are typically characterized by selective immunoreactivity with a particular heavy metal and a substantially lower immunoreactivity with other similarly structured heavy metals. Preferably, the monoclonal antibodies have an association constant for the selected heavy metal that is at least about 10,000 fold greater than the association constant for any similarly structured heavy metal. With respect to heavy metal cations, the especially preferred IgM and IgA classes of monoclonal antibodies of the present invention exhibit discriminatory dissociation constants of about $10^{-6}M$ to about $10^{-12}M$. Examples include monoclonal antibodies of the IgM class which are produced by hybridomas 6B11, 1254, 7D10, 4E8, 8E7, 14F11, 10G5 and 14G11 and have a dissociation constant for lead cation of less than about $10^{-9}M$ but do not bind cadmium, copper, zinc, nickel and cobalt cations to any appreciable extent. Other examples include monoclonal antibodies of the IgM and IgA classes which are produced by hybridomas derived from the spleen cells of a mammal injected with a solution of antibodies capable of immunoreacting with a lead cation. Suitable examples include monoclonal antibodies of the IgM class which are produced by hybridomas 13D10, 2E7, and 6F5. Monoclonal antibodies produced by hybridoma 11D11, 2B6, 13E8 and 8E7 are examples of antibodies of the IgA class which are capable immunoreacting with a lead cation.

Immunogen Compounds

The immunogen compounds for generation of the specific immunogenicity of the monoclonal antibodies are based upon the hapten-carrier concept. The present invention, however, broadens this concept so that the hapten is coordinated at the end of a spacer arm covalently bonded to the carrier. The spacer arm is adapted so as to be semi-rigid rigid and to hold the heavy metal in an exposed position relative to the carrier. This arrangement is also adapted to maintain the heavy metal in a substantially exposed and preferably, essentially completely exposed state. These factors combine substantially to avoid chelating, covering or inclusion of the heavy metal by the spacer arm and/or the carrier.

The spacer arm, as characterized above, may be an oligopeptide, an aliphatic compound, or an aliphatic fragment. In the latter two instances, the aliphatic compound or fragment may be covalently bonded to the carrier by means of a Schiff base reaction with an aldehyde group, an amide formation reaction with an amine or carboxylic acid group using a peptide activator such as carbodiimide, acid chloride and the like, an ester formation reaction with a hydroxyl or carboxylic acid group using a Schotten Bauman reaction, or azide or acid catalysis reaction, a sulfide reaction using a sulfide coupling agent, or other known coupling reactions for joining organic molecules to proteins. See for example Kabat, E.A., *Structural Concepts In Immunology and Immunochemistry*, 2nd Ed., Holt, Rinehart and Winston, New York, 1976 (a review text of such methods) and Jaime Eyzaguirre, *Chemical Modification of Enzymes: Active Site Studies*, John Wiley & Sons (1982), the disclosures of which are incorporated herein by reference. The oligopeptide, aliphatic compound or fragment will contain backbone groups which provide semi-rigidity to the spacer arm. Preferred groups for developing this semi-rigidity include peptide bonds, olefin bonds, olefinic conjugated systems, ester groups and enone groups. Optionally, and especially where immunogenicity of the heavy metal appears difficult to generate, one or more aromatic rings can be incorporated into the spacer arm to stimulate the development of an immune response.

In general, the oligopeptide spacer arm has the following formula:

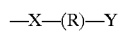

wherein X is a coupling group that will bond to the carrier, R is one or more amino acid residues and Y is the Lewis Acid or Base group(s) for heavy metal coordination.

In general, the aliphatic compound or fragment spacer arm has the following formula:

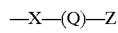

wherein X is a coupling group that will bond to the carrier, Q is a semirigid aliphatic moiety containing ester, amide, keto, olefin or aromatic groups and the like, and Z is a Lewis acid or Base group(s) for heavy metal coordination.

The oligopeptide or aliphatic compound is used as the spacer arm to coordinate a metal cation. In this instance, the pendent Lewis base groups will preferably be positioned at the spacer arm end remote from the carrier. These Lewis base groups function as the coordination site or sites for the metal cation. It is preferable that the deformability of the electron shells of the Lewis base groups and the metal cations be approximately similar. Accordingly, sulfur groups can serve as the Lewis base groups when the metal cations are transition metals or inner transition elements.

The carrier of the immunogen compound is a large biopolymer that is known to participate in the development of hapten antigenicity. Blood serum proteins, amylopectins, polysaccharides, fetal serum components, biologically acceptable natural and synthetic proteins and polyamides such as polyglycine can serve as the carriers. Preferred carriers include serum and tissue proteins. Examples are keyhole limpet hemocyanin (KLH) and bovine serum albumin (BSA). Other examples include ovalbumin and chicken gamma globulin. These carriers have sites for coordinate bonding of the spacer arm. Such sites are preferably populated by amine groups, carboxylic acid groups, aldehyde groups and/or alcohol groups.

Production of Hybridomas

The production of hybridomas according to the invention generally follows the Kohler, Milstein technique cited supra. Many heavy metals, however, toxify the mammalian system being used as a source of immune cells. This effect makes it important to determine the highest allowable dose of heavy metal and/or immunogen compound that can be used over a substantially long period of time without killing the host. Pursuant to the Kohler, Milstein technique, immunization of the mammalian host may be accomplished within this dose parameter by subcutaneous or intraperitoneal injection of the immunogen compound in adjuvant. Administration is repeated periodically and preferably for at least four injections. Three days before the spleen is removed, a priming injection of immunogen compound is again administered.

After separation, the spleen cells are fused with immortal mammal cells such as mouse myeloma cells using the techniques outlined by Kohler and Milstein. Polyethylene glycol (PEG) or electrical stimulation will initiate the fusions.

The fused cells are then cultured in cell wells according to culture techniques known in the art. Cellular secretions in the culture medium are tested after an appropriate time for the presence of the desired cellular products.

The induction of antibodies to heavy metals in a mammalian host may also be accomplished by subcutaneous or intraperitoneal injection of a lead cation monoclonal antibody solution in an adjuvant. These antibodies are typically derived from another animal of the same species. The spleen cells are then isolated and fused with immortal mammalian cells as described above. As before, the fused cells are cultured and the cellular secretions are examined for the presence of the desired antibodies ("Group 3 monoclonal antibodies").

The latter technique based on the induction of antibodies using a second lead cation antibody may be more efficient than the method based on the injection of a Pb(II)/glutathione/carrier immunogen compound into a mouse. Table 1 herein shows the relative success rate for induction of lead cation antibodies using the two techniques. The results shown in Table 1 demonstrate that the rate of generating lead cation monoclonal antibody producing hybridomas formation derived from injection of the 1254 mAb was greater than twenty fold more efficient than the method based on injection of the VA/glutathione/Pb(II) immunogen compound. In fact, a single set of fusions of spleen cells from animals injected with the 1254 mAb produced more lead cation antibodies than the total number of lead cation antibodies produced by five sets of fusions of spleen cells induced with the immunogen compound.

Selection Technique

The selection technique for identifying the appropriate monoclonal antibody is an important aspect for determining the immunospecificity desired according to the invention. The selection techniques according to the invention call for determining the binding affinity of the hybridoma cellular products against the heavy metal and against cross-reactive controls. In particular, hybridoma culture fluid is tested in screening assays against the heavy metal, the carrier, the carrier-spacer arm product and the immunogen compound as well as optionally against the spacer arm-heavy metal coordinate. Screening assays can be performed by immunoenzymatic-assay, immunofluorescence, radioimmunoassay, immunoprecipitative assay or inhibition of biological activity.

The hybridoma cultures selected will exhibit strong binding characteristics to the heavy metal (and immunogen compound) and will not bind with the spacer arm-carrier product or with the carrier itself.

Following the identification of cell cultures producing the desired monoclonal antibodies, subcloning to refine the selected culture can be performed. These techniques are known to those skilled in the art. See for example Goding, James Goding,*Monoclonal Antibodies: Principles and Practice,* 2nd Edition, Academic Press, San Diego, Calif. 1986, the disclosure of which is incorporated herein by reference. Briefly, the appropriately selected cell culture is separated into one cell units which are then recultured. The subclone cultures are then again tested for specific immunoreactivity, lack of cross-reactivity and the amount of monoclonal antibody secreted. Those subcultures exhibiting the highest amounts of secreted monoclonal antibody are chosen for subsequent pilot development.

Following the foregoing techniques, a number of hybridomas producing monoclonal antibodies to lead cations have been developed. Perpetual cell lines, designated 6B11, 1254 (8.15), 7D10, 4E8, 8E7, 17E5, 14F11, 10G5, 14G11 and 3H7, produce monoclonal antibodies to lead cations. The group of cell lines were developed by inoculation of mice with an OVA/glutathione/Pb(II) conjugate. The sensitivity of monoclonal antibodies produced by these hybridoma cell lines is shown in FIGS. 7 and 8. The sensitivity of mAb 3A6 (a monoclonal antibody specific for the PR8 influenza virus), which was included as a control, as anticipated, showed no sensitivity to Pb(II) (see FIG. 8). Monoclonal antibody 4A10 was derived from the spleen cells of a mouse injected with a mercury cation. The monoclonal antibodies produced by hybridoma 4A10 cross react with Pb(II) cations as well as immunoreacting with a mercury cation.

Using similar fusion and selection techniques, a number of hybridomas producing monoclonal antibodies to lead cations were developed by inoculation of mice with different lead cation monclonal antibodies ("Group 3 lead cation monoclonal antibodies"). Perpetual cell lines, designated 2B4, 2B6, 3B6, 13B7, 13B11, 16B11, 6C2, 14C6, 19C6, 11D11, 13D10, 2E7, 4E4, 12E5, 13E8, 13E7, 6F5, 1G4, 1G6, 6G2, and 13G9 were developed using this latter technique. The sensitivity of monoclonal antibodies produced by these hybridoma cell lines is shown in FIGS. 9–11. The set of Group 3 lead cation monoclonal antibodies exhibited lead sensitivity comparable to the "parent" Group 1 antibody, mAb 1254, and to other Group 1 lead cation monoclonal antibodies generated by injection of the OVA/glutathione/lead(II) immunogen compound.

The immunogenic host for these hybridomas was the BALB/c mouse and the fusion partner was chosen from the mouse myeloma cell lines P3X63-Ag8.653 or SP2/0. Immunizations to induce Group 1 lead cation antibodies were accomplished with the immunogen compound formed from ovalbumin, glutathione and lead(II) cation functioning as the heavy metal in complete Freund's adjuvant. Immunizations to induce Group 3 lead cation antibodies were accomplished with the lead cation monoclonal antibody designated 1254 ("mAb 1254") in an adjuvant. All of the cell lines mentioned above are maintained in culture medium and in frozen medium at liquid nitrogen temperature.

PCR Amplification

PCR amplification of Fd and κ regions from the spleen messenger RNA (mRNA) of a mouse immunized with BSA-glutathione-lead cation may be performed as described by Sastry et al., *Proc. Natl. Acad. Sci U.S.A.*, 86, 5728 (1989). The PCR amplification is performed with cDNA obtained by the reverse transcription of the mRNA with a primer specific for amplification of heavy chain sequences or light chain sequences.

The PCR amplification of mRNA isolated from spleen cells or hybridomas with oligonucleotides that incorporate restriction sites into the ends of the amplified product may be used to clone and express heavy chain sequences (e.g., the amplification of the Fd fragment) and κ light chain sequences from mouse spleen cells. The oligonucleotide primers, which are analogous to those that have been successfully used for amplification of $V_H$ sequences (see Sastry et al., *Proc. Natl. Acad. Sci U.S.A.*, 86, 5728 (1989)), may be used for these amplifications. Restriction endonuclease recognition sequences are typically incorporated into these primers to allow for the cloning of the amplified fragment into a λ phage vector in a predetermined reading frame for expression.

Expression of Fab Fragments on Phage Coat

Phage assembly proceeds via an extrusion-like process through the bacterial membrane. Filamentous phage M13 has a 406-residue minor phage coat protein (cpIII) which is expressed before extrusion and which accumulates on the inner membrane facing into the periplasm of *E. coli*. The two functional properties of cpIII, infectivity and normal (nonpolyphage) morphogenesis, have been assigned to roughly the first and second half of the gene. The N-terminal domain of cpIII binds to the F' pili, allowing for infection of *E. coli*, whereas the membrane-bound C-terminal domain, P198-S406, serves the morphogenic role of capping the trailing end of the filament according to the vectorial polymerization model.

A phagemid vector may be constructed to fuse the antibody Fd chain with the C-terminal domain of cpIII (see Barbas et al., *Proc. Natl. Acad. Sci. USA*, 88, 7978 (1991)). A flexible five-amino acid tether (GGGGS), which lacks an ordered secondary structure, may be juxtaposed between the expressed Fab and cpIII domains to minimize interaction. The phagemid vector may also be constructed to include a nucleotide coding for the light chain of a Fab fragment. The cpIII/Fd fragment fusion protein and the light chain protein may be placed under control of separate lac promoter/operator sequences and directed to the periplasmic space by pelB leader sequences for functional assembly on the membrane. Inclusion of the phage F1 intergenic region in the vector allows for packaging of single-stranded phagemid with the aid of helper phage. The use of helper phage superinfection may result in expression of two forms of cpIII. Consequently, normal phage morphogenesis may be perturbed by competition between the cpIII/Fd fragment fusion protein and the native cpIII of the helper phage for incorporation into the virion. The resulting packaged phagemid may carry native cpIII, which is necessary for infection, and the fusion protein including the Fab fragment, which may be displayed for interaction with an antigen and used for selection. Fusion at the C-terminal domain of cpIII is necessitated by the phagemid approach because fusion with the infective N-terminal domain would render the host cell resistant to infection. The result is a phage displaying antibody combining sites ("Phabs"). The antibody combining sites, such as Fab fragments, are displayed on the phage coat. This technique may be used to produce Phabs which display recombinantly produced Fab fragments (e.g., recombinantly produced Fab fragments that immunoreact with a lead cation) on the phage coat of a filamentous phage such as M13.

A phagemid vector (pComb 3) which allows the display of antibody Fab fragments on the surface of filamentous phage, has been described (see Barbas et al., *Proc. Natl. Acad. Sci. USA*, 88, 7978 (1991)). XhoI and SpeI sites for cloning PCR-amplified heavy-chain Fd sequences are included in pComb 3. SacI and XbaI sites are also provided for cloning PCR-amplified antibody light chains. These cloning sites are compatible with known mouse and human PCR primers (see, e.g., Huse et al., *Science*, 246, 1275–1281 (1989)). The nucleotide sequences of the pelB leader sequences are recruited from the λ HC2 and λ LC2 constructs described in Huse et al, ibid, with reading frames maintained. Digestion of pComb 3 encoding a selected Fab with SpeI and NheI permits the removal of the gene III fragment. Because SpeI and NheI produce compatible cohesive ends, the digested vector may also be religated to yield a phagemid that produces soluble Fab.

Phabs may be produced by overnight infection of phagemid containing cells (e.g., infected *E. coli* XL-1 Blue) yielding typical titers of $10^{11}$ cfu/mL. By using phagemids encoding different antibiotic resistances, ratios of clonally distinct phage may easily be determined by titering on selective plates. In single-pass enrichment experiments, clonally mixed phage may be incubated with an antigen-coated plate. Nonspecific phage will be removed by washing, and bound phage may then be eluted with acid and isolated.

Methods of Application

According to the invention, the metal binding polypeptide can be used to advantage for detection, neutralization, addition or removal of heavy metals from biological or inanimate systems. These methods apply to qualitative and quantitative analyses of minute concentrations of toxic metal cations, in aqueous liquid systems, in biological or environmental systems or in such compositions as perfumes, cosmetics, pharmaceuticals, health care products, skin treatment products, pesticides, herbicides, solvents used in the production of semi-conductor and integrated circuit components and production materials for electronic components. In each application, the presence of minute quantities of metallic cations could constitute deleterious contaminants. Their ready and early detection will avoid later production or regulatory set-backs.

Alternatively, the presence of minute quantities of heavy metals in certain instances may be desirable. For example, the presence of inorganic moieties in such mixtures as doping materials for semi-conductors and integrated circuits contributes to the properties of the product. Quality control of the presence and concentration of these heavy metals is essential for the functioning of the product. The detection methods of the invention enable ready and early measurement of the presence of such heavy metals and avoid later production or regulatory difficulties.

Heavy metals in biological or inanimate systems can also be removed by methods according to the invention. In the main, immobilization of the metal binding polypeptides on a solid support followed by its mixture with the materials of the biological or inanimate system will remove the heavy metals. In this instance, the immobilization of the monoclonal antibodies can be accomplished by techniques known to those of skill in the art. See, for example, *Affinity Chromatography*, C.R. Fowe & P.D.G. Sean, John Wiley & Sons, London 1974, the disclosure of which is incorporated herein by reference. Removal is accomplished by passing a fluid mixture of the system ingredients suspected of having the heavy metals over the immobilized metal binding polypeptides. Of course, the metal binding polypeptides are designed to be specific for the heavy metal sought to be removed.

An advantage of this method is the removal of undesirable heavy metals in the presence of similarly structured desirable metal species. For example, whole blood from a patient suffering from lead poisoning can be removed from the patient, optionally filtered to return the cellular blood components to the patient, and the serum or blood passed over immobilized metal binding polypeptides specific for the lead. The purified serum or blood can then be returned to the patient. The lead will be removed but other blood serum components such as zinc, calcium and the like will not.

Specific Applications

A particular application of the present invention contemplates a method for the production of monoclonal antibodies specific for the lead cation or another toxic, heavy metal cation. In accordance with this method, the heavy metal cation in question is combined into an immunogen compound as described above and suspended in an aqueous medium. A preferred protein carrier for the immunogen compound in this instance is an albumin, e.g., ovalbumin. keyhole limpet hemocyanin is also a preferred carrier. The preferred spacer arm in this instance is an oligopeptide which has sulfonate or carboxylate groups capable of coordinating with the heavy metal cation. The suspension of immunogen compound is used to immunize a host mammal such as a mouse following the techniques outlined above. The laboratory strain of mouse designated BALB/c is particularly preferred.

Spleen cells of the immunized host are collected and converted into a suspension. These spleen cells are fused with immortal cells as described above. Preferably, myeloma cells of the same animal species as the immunized host are used as the fusion partner. Typically, a cell fusion promoter such as polyethylene glycol is employed to cause formation of the hybridoma cells. The hybridoma cells are diluted and cultured in a medium which does not allow for the growth of unfused cells.

The monoclonal antibodies produced and secreted by the hybridomas are thereafter assayed for the ability to bind immunologically with the heavy metal cations used for immunization. The antibodies are further selected for lack of cross-reactivity with carrier, with carrier-spacer arm and with similar metallic cations. The preferred assay method in this context is an enzyme-linked immunosorbent assay.

The resulting monoclonal antibodies are specific for heavy metal cations and exhibit strong immunoreaction to the heavy metal cations in the presence of spacer arm or the spacer arm-carrier composition. Preferred monoclonal antibodies are selectively immunoreactive with lead cations.

The present invention also provides methods and kits for detecting the presence of a toxic heavy metal cation such as a lead cation. The methods and kits include a metal binding polypeptide which selectively binds the heavy metal.

According to an embodiment of a method for detecting the presence of a specific heavy metal cation, an immobilized coordinating compound is combined with the unknown mixture containing the toxic heavy metal cation. The heavy metal cation complexes with the coordinating compound and is immobilized thereto. Removal of the non-immobilized components leaves the immobilized toxic heavy metal cation. Addition of the metal binding polypeptide specific for the targeted heavy metal cation forms an immobilized cation-metal binding polypeptide conjugate. Its presence and concentration can be assayed by an ELISA technique or other tagging or visualization technique known to those of skill in the art. In this process, of course, non-immobilized metal binding polypeptide is removed before the assay is conducted.

A kit for quantitatively measuring the presence of a heavy metal cation is a further aspect of the invention. The kit includes a metal binding polypeptide specific for the toxic metal cation in question. The metal binding polypeptide is preferably metered into several aliquots of varying, known concentration. The kit may also include the immobilized coordination compound, preferably, attached to a solid support such as the well of a microtiter plate or a chromatographic material. The kit also typically includes a visualization or tagging assay material for determination of the presence of the metal binding polypeptide-heavy metal cation conjugate. If desired, a meter or other device for detecting and signaling the level of visual or other reading from the assay may also be included.

The invention will be further characterized by the following examples. These examples are not meant to limit the scope of the invention which has been fully set forth in the foregoing description. Variation within the concepts of the invention are apparent to those skilled in the art.

EXAMPLE 1

Lead Cation Monoclonal Antibodies

A. General Procedures

1. Generation of Hybridomas via Injection of OVA/glutathione/Pb(II)

Hybridoma antibodies were produced from the spleen cells of BALB/c mouse that had received multiple injections of lead(II) cations reacted with glutathione to produce a lead cation coordinate covalent compound, which was covalently bound to ovalbumin ("OVA/glutathione/Pb(II) antigen"). Glutathione is a three amino acid residue peptide having one reactive sulfhydryl group which forms a coordinate bond with lead cations. The OVA/glutathione/Pb(II) antigen in complete Freund's adjuvant was utilized to assist in the elicitation of an immune response in the host animal.

Of hybridomas isolated, some were determined to be producing monoclonal antibody specific for glutathione. In addition, other hybridomas (6B11, 1254, 8E7, 10G5 and 14F11) were producing monoclonal antibodies that were strongly positive against glutathione-lead cation but negative against glutathione without lead cation. These antibodies were subcloned by the process of limiting dilution for further characterization.

ELISA Analysis for Hybridoma Antibodies Immunoreactive With Glutathione-Lead Cations Microtiter plates (EIA/RIA grade) were treated with BSA-glutathione, blocked with 1% polyvinyl alcohol in phosphate-buffered saline ("PBS") and used for the ELISA. One hundred microliters of lead nitrate (100 ppm in 100 Molar Hepes pH 7.2) was added to the wells and incubated for 30 minutes. The plates were washed three times with PBS containing 0.1% Triton X-100, and then the hybridoma culture supernatant was added for 30 minutes at room temperature. After washing the wells, goat anti-mouse antibodies conjugated to horseradish peroxidase were added. Following incubation for 30 minutes at room temperature, the plates were washed with PBS containing 0.1% Triton X-100, and 100 ul of ABTS peroxidase substrate was added to each well. After 15 min at room temperature the absorbance of each well was read at 405 nanometers. In addition, the frozen hybridoma samples have been thawed from liquid nitrogen and assayed for persistence of antibody secretion after thawing.

2. Determination of Lead-Cation Specific Monoclonal Antibodies

The monoclonal antibodies may be assayed with various other metals for inhibition of binding of the monoclonal antibodies to lead cations. The cationic metals assayed may include the ions of zinc, copper, cadmium, nickel, and arsenic. For instance, the inhibition of the binding of a monoclonal antibody which immunoreacts with immobilized glutathione-lead cations by various concentrations of divalent cations may be examined. Metal ions at the indicated concentrations are incubated with culture fluid from the antibody in an ELISA plate. The absorbance at 405 nm may be determined for each sample, and the percent inhibition of each metal ion concentration determined by the formula given above.

Further analysis of the monoclonal antibodies can establish if the antibodies are specific for the lead cations per se and that glutathione is not needed for the monoclonal antibodies to react with and bind to the lead cations. The monoclonal antibodies may also be assayed against BSA-glutathione, BSA-glutathione-lead cations, and BSA-lead cations. Comparison with a negative control consisting of a monoclonal antibody specific for an unrelated antigen permits a determination of whether the monoclonal antibodies bind to lead cation in the absence of glutathione.

PBS containing metal ions at the indicated concentrations may be added to microtiter wells to which BSA-glutathione has been absorbed. After incubation at room temperature for 30 minutes, the plates are washed to remove unbound metals, and the plates are used for a standard ELISA to detect lead cations.

B. Particular Preparations

1. Linkage of Lead Cations to Protein Carriers

To prepare antigen for injection and immunoassay, 132 mg $Pb(NO_3)_2$ (400 $\mu$mol), 61 mg glutathione (200 $\mu$mol) and 54 mg NaCl were dissolved in 10 mL of water. After cold ethanol (30 mL) was added, the resulting mixture was incubated for 30 minutes at 0° C. The reaction mixture was centrifuged at 10,000 g for 30 minutes, and the pellet was washed with 30 mL of cold ethanol. The pellet was dissolved in 200 mL of 40% dimethylformamide pH 4.8, containing 200 mg of 1-ethyl-3-(3-dimethylaminopropyl)-carbodiimide, and 1 g of either bovine serum albumin or OVA was added to the solution. The reaction mixture was stirred at room temperature overnight. The mixture was then centrifuged as above, resuspended in PBS, and dialyzed overnight at 4° C. against 4 liters of PBS.

2. Immunization of BALB/c Mice

Multiple injections of the antigen prepared with 10 ug of protein per injection were made into BALB/c mice. Lead cation-glutathione-OVA emulsified in Freund's adjuvant was employed as the antigen. Complete adjuvant was used for the first two injections, while incomplete adjuvant was used for all subsequent injections. After the fourth injection, a drop of blood from the tail of each mouse was collected separately in 0.5 mL of PBS, and each sample was assayed by ELISA for the presence of antigen-specific antibody. The mice used for hybridoma production received an intraperitoneal injection consisting of 10 ug of antigen in PBS 3–4 days before cell fusion.

3. Hybridoma Production

The spleen was removed aseptically from a mouse, and the cells were isolated by placing the spleen in 5 mL of sterile PBS and teasing it with two sterile, 18-gauge hypodermic needles. The cell suspension was added to an empty sterile, conical, 15-mL centrifuge tube and tissue fragments were allowed to settle for 1–2 minutes. The cells still in suspension were placed in a tube similar to that above and centrifuged at 300 g for 10 minutes at room temperature. The cells were then washed 3 times by centrifugation in serum-free DMEM (Dulbecco's modified Eagle's medium). Spleen cells were co-pelleted with P3X63-Ag8.653 myeloma cells at a ratio of 4 spleen cells to 1 myeloma cell. The supernatant fluid was removed, and the pellet was suspended in 1 mL of 35% polyethylene glycol for 1 minute. The polyethylene glycol was gradually diluted by addition of increasing amounts of serum-free DMEM over a period of 15 minutes. The cells are then suspended in HAT medium (*Monoclonal Antibodies,* Kennett, McKean, Backitt, eds., Plenum Press (1981)) at a concentration of $2\times10^5$ myeloma cells per mL, and 100 $\mu$L of the suspension were added to each well of 5 separate 96-well microtiter plates. The plates were incubated in 10% $CO_2$ at 37° C. for one week. At that time, half of the culture fluid was withdrawn from each well and replaced by 2 drops of fresh HT medium (HAT medium without aminopterin), and the plates were incubated as above for another week. Then, approximately 100 $\mu$L of culture fluid was taken from each well containing macroscopically visible cell growth, and the ELISA technique described infra was used for identification of those culture fluids containing lead cation-specific antibodies.

4. Enzyme-Linked Immunosorbent Assay (ELISA)

Polyvinyl chloride microtiter assay plates may be coated with antigen by addition of 50 $\mu$l of lead cation-glutathione-BSA or glutathione-BSA at a concentration of 5 ug/mL in PBS to each well of the plate. The plates are allowed to incubate at room temperature overnight to allow the antigen to dry on the plate. Next day the plates are blocked by addition of 200 $\mu$L of 1% polyvinyl alcohol ("PVA") in PBS to each well; the addition of the PVA blocks the remaining protein-binding sites. The plates are incubated for 30 min at room temperature, then washed 3 times with ELISA wash (PBS with 0.1% of Triton X-100), 3 times with milliQ water. A 100 ppm solution of lead in 100 mM Hepes at pH 7 is then added to the wells (100 $\mu$L/well and allowed to incubate for 30–60 minutes at room temperature.

Fifty microliters of culture fluid to be assayed for the presence of antigen-specific antibody may be added to the appropriate well, and the plates are incubated at room temperature for 2 hours. The plates are again washed 3 times with ELISA wash, and 50 $\mu$L of goat anti-mouse serum (Cooper Biomedical) diluted 1:1000 in 2% BSA in PBS are added to each well. After incubation and washing as above, 50 µL of rabbit anti-goat serum conjugated to alkaline phosphatase (Sigma) diluted 1:1000 in 50 mM Tris-HCl, pH 8.0, containing 1 mM $MgCl_2$, 5% BSA and 0.04% $NaN_3$, are added to each well. After being incubated and washed as above, 150 µL of phosphatase substrate (0.4 mM dinitrophenyl phosphate in 1 M diethanolamine, pH 9.8, containing 25 mM $MgCl_2$) are added to each well.

The enzyme catalyzed conversion of dinitrophenol phosphate to dinitrophenol is typically allowed to proceed at room temperature for 30–60 minutes. The absorbance of each well at 405 nm (dinitrophenol) may be measured with a UV/Vis spectrometer.

The use of other enzymes as sensors is also possible provided that such enzymes can be linked to an appropriate antibody, and catalyze a reaction which produces a color change. For example, beta galactosidase, urease, or horseradish peroxidase could be utilized in this context.

5. Binding of Lead Cations to Immobilized Coordinating Spacer Arms

One hundred microliters of BSA-glutathione at a concentration of 5 ug/mL were added to the wells of a microtiter plate and allowed to dry overnight. The plates were then blocked with PVA as above. One hundred microliters of PBS containing a known concentration of lead cations were added to triplicate wells on the plate, which were then incubated at room temperature for 30 minutes. After this incubation period the plates are washed with ELISA wash to remove unbound metal ions and then used in the standard ELISA to measure reactivity with a lead cation-specific antibody.

6. Assay of Lead Cation-Specific Antibodies Against BSA Glutathione, BSA Glutathione-Lead and BSA-Lead Lead cation specific antibodies secreted from hybridomas such as 6B11, 1254, 8E7, 10G5 and 14F11 were assayed against BSA-glutathione and BSA-glutathione-lead cation. The results established that all five antibodies immunoreacted with BSA-glutathione that had bound lead, and did not immunoreact with BSA-glutathione lacking lead.

EXAMPLE 2

Nucleotides Coding for Heavy Chain Fd Fragments and Light Chains from Lead Cation Monoclonal Antibodies Synthesis of Nucleotides Encoding the Heavy and Light Chain Variable Regions of the Lead-Cation Antibodies RNA was isolated from hybridoma cells with guanidine isothiocyanate (Evans et al., *BioTechniques*, 8, 357 (1990)), and enriched for poly(A) +RNA by passage over a poly(dT)-cellulose column (Aviv et al., *Proc. Natl. Acad. Sci. USA*, 69, 1408 (1972)). First-strand cDNA synthesis was catalyzed by MuLv reverse transcriptase with a Promega RiboClone kit, according to the manufacturer's directions. The primers used for cDNA synthesis were complementary to the 5' end of the $C_H1$ domain of the heavy chain expressed by the hybridoma of interest, or to the 5'end of the Cκ domain. The following primers were used for cDNA synthesis:

KAPPA Primer—Light Chain 5 1-GAAGATCTAGACTTACTATGCAGCATCAGC-3¹
(SEQ ID NO:41)

MU primer—Heavy Chain

5-AGGAGACTAGTGGTTACTAATTTGGGAAGGACTG-3
(SEQ ID NO:42)

Amplification of Antibody Variable Regions by Polymerase Chain Reaction

The primer used for cDNA synthesis of the variable region of a particular antibody polypeptide chain was also used for PCR amplification of that variable region, in conjunction with an appropriate V-region primer as described in Huse et al., *Science*, 246, 1275 (1989). The PCR was performed as described in Sastry et. al., *Proc. Natl. Acad. Sci. USA*, 86, 5728 (1989).

Sequence Determination of Nucleotides Encoding the Heavy and Light Chain Variable Regions of the Lead Cation Antibodies The PCR amplified nucleotide sequences encoding the heavy and light chain variable regions of the lead cation antibodies were cloned into Bluescript (Stratagene, La Jolla, Calif.). The sequences of these nucleotides were determined by the dideoxy chain termination method (Sanger et al., *Proc. Natl. Acad. Sci. USA*, 74, 5463 (1977)). The sequences of at least three PCR products for each heavy and light chain were determined to allow detection of incorporation errors by Taq polymerase. The nucleotide and deduced amino acid sequences of the heavy and light chain variable regions of the lead-specific antibodies are shown in FIGS. 1A–1B and 2.

FIGS. 1A–1B depict the nucleotide and deduced amino acid sequences for the heavy chain variable regions of a number of monoclonal antibodies that immunoreact with a lead cation. The following sequences are shown:

the heavy chain variable region nucleotide acid sequence (SEQ. ID NO.: 1) and deduced amino acid sequence (SEQ. ID NO:2) for monoclonal antibody 6B11;

the heavy chain variable region nucleotide sequence (SEQ. ID NO. 3) and deduced amino acid sequence (SEQ. ID NO:4) for monoclonal antibody 1254;

the heavy chain variable region nucleotide sequence (SEQ. ID NO:5) and deduced amino acid sequence (SEQ. ID NO:6) for monoclonal antibody 8E7;

the heavy chain variable region nucleotide sequence (SEQ. ID NO:7) and deduced amino acid sequence (SEQ. ID NO:8) for monoclonal antibody 10G5; and the heavy chain variable region nucleotide sequence (SEQ. ID NO:9) and deduced amino acid sequence (SEQ. ID NO:10) for monoclonal antibody 14F11.

FIG. 2 depicts the nucleotide and deduced amino acid sequences for the light chain variable regions of a number of monoclonal antibodies which immunoreact with a lead cation. The following sequences are shown:

the light chain variable region nucleotide sequence (SEQ. ID NO:11) and deduced amino acid sequence (SEQ. ID NO:12) for monoclonal antibody 6B11;

the light chain variable region nucleotide sequence (SEQ. ID NO:13) and deduced amino acid sequence (SEQ. ID NO:14) for monoclonal antibody 1254; and the light chain variable region nucleotide sequence (SEQ. ID NO:15) and deduced amino acid sequence (SEQ. ID NO:16) for monoclonal antibody 14F11.

FIGS. 3A–3B depict the nucleotide and deduced amino acid sequences for the heavy chain variable regions of a number of monoclonal antibodies that immunoreact with a lead cation. The following sequences are shown:

the heavy chain variable region nucleotide acid sequence (SEQ. ID NO:17) and deduced amino acid sequence (SEQ. ID NO:18) for monoclonal antibody 13D10;

the heavy chain variable region nucleotide sequence (SEQ. ID NO:19) and deduced amino acid sequence (SEQ. ID NO:20) for monoclonal antibody 11D11;

the heavy chain variable region nucleotide sequence (SEQ. ID NO:21) and deduced amino acid sequence (SEQ. ID NO:22) for monoclonal antibody 14G11;

the heavy chain variable region nucleotide sequence (SEQ. ID NO:23) and deduced amino acid sequence (SEQ. ID NO:24) for monoclonal antibody 6F5;

the heavy chain variable region nucleotide sequence (SEQ. ID NO:25) and deduced amino acid sequence (SEQ. ID NO:26) for monoclonal antibody 7D10; and the heavy chain variable region nucleotide sequence (SEQ. ID NO:27) and deduced amino acid sequence (SEQ. ID NO:28) for monoclonal antibody 4E8.

FIG. 4 depicts the nucleotide and deduced amino acid sequences for the light chain variable regions of a number of monoclonal antibodies which immunoreact with a lead cation. The following sequences are shown:

the light chain variable region nucleotide sequence (SEQ. ID NO:29) and deduced amino acid sequence (SEQ. ID NO:30) for monoclonal antibody 10G5;

the light chain variable region nucleotide sequence (SEQ. ID NO:31) and deduced amino acid sequence (SEQ. ID NO:32) for monoclonal antibody 2E7; and the light chain variable region nucleotide sequence (SEQ. ID NO:33) and deduced amino acid sequence (SEQ. ID NO:34) for monoclonal antibody 7D10;

the light chain variable region nucleotide sequence (SEQ. ID NO:39) and deduced amino acid sequence (SEQ. ID NO:40) for monoclonal antibody 6F5.

FIG. 5 depicts the nucleotide and deduced amino acid sequences for the heavy chain variable regions of the monoclonal antibody 2B4 that immunoreacts with a lead cation. The following sequences are shown:

the heavy chain variable region nucleotide sequence (SEQ. ID NO:35) and deduced amino acid sequence (SEQ. ID NO:36) for monoclonal antibody 2B4.

FIG. 6 depicts the nucleotide and deduced amino acid sequences for the heavy chain variable regions of the monoclonal antibody 2E7 that immunoreacts with a lead cation. The following sequences are shown:

the heavy chain variable region nucleotide sequence (SEQ. ID NO:37) and deduced amino acid sequence (SEQ. ID NO:38) for monoclonal antibody 2E7.

As can be seen in the above-described amino acid sequences, (see, for example, FIGS. 2 and 4) most of the light chains of the lead-reactive monoclonal antibodies are members of the $V_k32$ light chain family, having a motif of four carboxylic acid-containing residues, e.g., glutamic acid and/or aspartic acid residues, in a stretch of five amino acids in the CDR1 region (amino acid residues 28, 30, 31 and 32; numbered according to Kabat). The interaction of the light chain with a lead cation was modeled using molecular dynamics calculations which constrained the light chain backbone to an antibody template and searched for the best fit conformation of the side chains carboxylic acid groups with the lead cation. The molecular modeling results indicate that the side chain carboxyl groups of two of the aspartic acid residues, residues 30 and 32, are positioned at the appropriate distance to form coordinate interactions with the lead cation. In addition, the modeling indicated that the aspartic acid residue present at position 92 in the CDR3 region of the light chain sequences was also situated to coordinately interact with the lead cation. Based on the modeling results, the present lead binding polypeptide preferably include a light chain variable region with a carboxylic acid side chain group-containing amino acid residue in at least two of positions 30, 32 and 92. More preferably, the light chain variable region includes aspartic acid residues at all three of positions 30, 32 and 92.

As described in the Examples, regardless of the specific antigen used for induction of lead-specific antibodies (e.g., anti-lead antibody or lead-containing complex), the majority of the resulting lead-reactive monoclonal antibodies contained light chains of the $V_k32$ family.

EXAMPLE 3

Expression of Fusion Proteins Including Heavy Chain Fd Fragments and Light Chains from Lead Cation Monoclonal Antibodies 1. Vector Construction The pelB leader sequences and cloning sites for the heavy-chain fragment and light chain may be derived from phagemids excised from λ Hc2 and λ Lc2 vectors as described in Huse, et al., *Science*, 246, 1275–1281 (1989). The sequences may be modified to remove a redundant SacI site from Hc2 phagemid and a SpeI site from the Lc2 phagemid. The combinatorial phagemid vector pComb is constructed from these two modified phagemids by restricting each with ScaI and EcoRI and combining them in a ligation reaction. Recombinants are screened for the presence of two NotI sites yielding the combinatorial vector pComb. The tether sequence GGGGS and gIII fragment (gene coding for coat protein III of filamentous phage M13 (see Barbas, et al., *Proc. Natl. Acad. Sci. USA*, 88, 7978 (1991)) from SpeI to NheI are the product of PCR of M13mp18 (Yanisch-Perron, et al., *Gene*, 33, 103–119 (1985)) using the oligonucleotides 5'-GAGACGACTAGTGGTGGCGGTGGCTCTCCATTCG TTTGTGAATATCAA-3' (SEQ ID NO:43) and 5'-TTACTAGCTAGCATAATAACGGAATACCCAAAAG AACTGG-3' (SEQ ID NO:44) as reported in Barbas, et al., *Proc. Natl. Acad. Sci. USA*, 88, 7978 (1991).

The lacZ promoter, operator, and Cap-binding site controlling light chain expression are the product of PCR with M13mp18 using oligonucleotides 5'-TATGCTAGCTAGTAACACGACAGGTTTCCCGACT GG-3' (SEQ ID NO:45) and 5'-AGCTTTGAATTCGTGAAATTGTTATCCGCT-3' (SEQ ID NO:46) as reported in Barbas et al., ibid. The PCR fragments encoding the gIII fragment and lacZ promoter are spliced by PCR overlap extension (see Horton et al., *Gene*, 77, 61–68 (1989)). The resulting product is digested with SpeI and EcoRI and ligated into the corresponding sites of pcomb to yield pComb 3'. Finally, pComb 3' is digested with XhoI and SpeI and ligated with the corresponding 51-base-pair (bp) stuffer from pBluescript (see Short, et al., *Nucleic Acids Res.*, 16, pp. 7583–7600 (1988)) (Stratagene) to yield pComb 3, an ampicillin-resistant phagemid.

2. Expression of Nucleotides on M13 Phage Coat Phage Production

A pComb 3 phagemid including a recombinantly produced Fab fragment that immunoreacts with a lead cation may be transformed into *E. coli* XL1-Blue cells. The transformed *E. coli* XL1-Blue cells may be grown in super broth medium (SB; 30 g of tryptone, 20 g of yeast extract, 10 g of Mops per liter, pH 7) at 37° C. supplemented with tetracycline at 10 µg/ml and carbenicillin at 50 µg/mL or chloramphenicol at 30 µg/mL. Cultures are grown to an $OD_{600}$ of 0.4 and infected with VCSM13 helper phage (phage to cell ratio, 20:1) and grown an additional hour. After one hour kanamycin is added (70 µg/mL), and the culture is incubated overnight at 30° C. Phage may be isolated from liquid culture by polyethylene glycol 8000 and NaCl precipitation as described in Cwirla, et al., *Proc. Natl. Acad. Sci. USA*, 87, pp. 6378–6382 (1990). Phage pellets may be resuspended in phosphate-buffered saline (10 mM phosphate, pH 7.2, 150 mM NaCl) and stored at −20° C.

3. Single-Pass Enrichment Experiments

Phage expressing lead cation binding Fab fragments on their surface may be enriched by a modification of the panning procedure described by ParmLey, et al., *Gene*, 73, pp. 305–318 (1988). A single well of a microtiter plate (Costar 3690) is coated overnight at 4° C. with 25 µL of BSA-glutathione-lead cation at 2 mg/mL in 0.1 M bicarbonate, pH 8.5. The well is washed once with water and blocked by filling the well with Blotto (1% (wt/vol) PVA in phosphate-buffered saline) and incubating the plate at 37° C. for one hour. Blocking solution is shaken out, and 50 µl of clonally mixed phage (typically $10^{11}$ colony-forming units (cfu)) is added, and the plate is incubated for an additional 2 hr at 37° C. Phage are removed, and the well is washed once with distilled water. The well is washed 10 times with TBS/Tween solution (50 mM Tris-HCl, pH 7.5, 150 mM NaCl, 0.05% Tween 20) over a period of one hour at room temperature. The well is washed once more with distilled water, and adherent phage are eluted by adding 50 µL of elution buffer (0.1 M HCl, adjusted to pH 2.2 with glycine), and incubation at room temperature for 10 min. The eluate is removed and neutralized with 3 µL of 2 M Tris base. The initial phage input ratio may be determined by titering on selected plates. The final phage output ratio may be determined by infecting 1 mL of logarithmic phase XL1-Blue cells with the neutralized eluate for 15 min at room temperature and plating equal aliquots on selective carbenicillin and chloramphenicol plates.

4. Lead Cation-ELISA for Phabs

Equal plaque forming units from Phabs obtained from cultures of *E. coli* XL1-Blue cell may be transformed with a phagemid including a recombinantly produced Fab fragment that immunoreacts with a lead cation incubated at 37° C. for two hours on BSA-Glutathione ELISA plates with or without lead nitrate. A rabbit anti-M13 antiserum is typically used as a second antibody followed by affinity-purified goat-antirabbit serum conjugated with peroxidase. 2,2′-Azino-Di-[3-ethylbenzthiazoline sulfonate] (ABTS) may be used as peroxidase substrate. The results are typically expressed as absorbance at 405 nanometers.

5. pComb3 Phagemid Expressing 1254 Light Chain

Using the methods described above, a pComb3 phagemid expressing only the light chain of monoclonal antibody 1254, without any accompanying heavy chain, was constructed. Two copies of the 1254 light chain sequence were cloned into the phagemid. Using the ELISA assay described above, the phagemid reacted with lead, demonstrating that the light chain of the antibodies is sufficient for lead binding.

EXAMPLE 4

Group 3 Lead Cation Monoclonal Antibodies

1. Generation of Hybridomas via Injection of Lead Cation Monoclonal Antibody 1254

Group 3 antibodies were produced by injecting mice with the Group 1 lead cation monoclonal antibody, mAb 1254 (mAb 8.15). The mice were injected biweekly with 50 µg of antibody emulsified in Freunds complete adjuvant and bled seven days after each injection. The mice were bled by nicking the tail and collecting 50 µl of blood, which was diluted to 500 µl in phosphate buffered saline (PBS). The serum was tested using the same ELISA procedure as for screening the fusions (described below). The spleen cells of the mice were then used for production of hybridoma monoclonal antibodies (mAb's) as described below.

Fusion Procedure for Hybridoma Production

A mouse was sacrificed by cervical dislocation, and its spleen was removed aseptically. A single cell suspension was prepared from the spleen, and the cells were washed three times in serum-free Dulbecco's modified Eagle's medium (DMEM) by centrifugation at 400× g for 10 minutes, with 10 ml of DMEM per wash. The number of viable spleen cells was determined by trypan blue exclusion with a hemacytometer. The spleen cells were then mixed with SP2/0 myeloma cells at a ration of 4 spleen cells:1myeloma cell. The SP2/0 cells had previously been washed three time with serum-free DMEM as described above for the spleen cells.

The cell mixture was centrifuged as above, and the cell pellet was resuspended in 500 µl of 50% polyethylene glycol (PEG 1500, Sigma Chemical Co., St. Louis, Mo.), which was added over a one-minute period. The cell suspension was stirred for an addition minute, followed by addition of 10 ml of serum-free DMEM over the next two minutes. After stirring for an additional minute, the cells were centrifuged at 400× g for 10 minutes, and the pellet was resuspended in HAT medium to a final concentration of $1 \times 10^7$ spleen cells/ml. Two hundred microliters of the cell suspension was added to each well of the appropriate number of 96-well microtiter plates, and the fusion was incubated at 37° C. in an atmosphere of 10% $CO_2$, 90% air. All reagents and supplies used in this procedure were sterile and at room temperature.

Culture media

All culture media was filtered through a 0.2 µm pore size filter (Nalgene).

A. Complete media

Add the following to 500 milliliters of DMEM (Gibco):
10% of complement free (56 C for 1 hour) bovine calf serum (Hyclone)
45 millimolar of sodium pyruvate (Sigma)
200 millimolar of L-glutamine (Sigma)
0.1% of gentamicin (Gibco)

B. HT media

Add the following to 500 milliliters of DMEM:
20% of complement free (56° C. for 1 hour) fetal clone (Hyclone)
45 millimolar of sodium pyruvate (Sigma)
200 millimolar of L-glutamine (Sigma)
10 millimolar of hypoxanthine (Sigma)
1.5 millimolar thymidine (Sigma)
100 millimolar oxaloacetate (Sigma)
0.1% of gentamicin (Gibco)

C. HAT media

Add the following to 500 milliliters of DMEM:
20% of complement free (56 C for 1 hour) fetal clone (Hyclone)
40 micromolar aminopterin (Sigma)
45 millimolar of sodium pyruvate (Sigma)
200 millimolar of L-glutamine (Sigma)
10 millimolar of hypoxanthine (Sigma)
1.5 millimolar thymidine (Sigma)
100 millimolar oxaloacetate (Sigma)
20 I.U./milliliter of bovine insulin (Sigma)
0.1% of gentamicin (Gibco)

2. Identification of Lead-Specific Antibodies by ELISA

An amino acid polymer consisting of glutamic acid, lysine, and tyrosine at a ratio of 6:3:1 respectively ("EKY polymer"; Sigma Chemical Co.) was prepared as a 50 µg/ml solution in PBS. One hundred microliters of the EKY polymer solution was added to each well of a high-binding polystyrene plate (Corning Costar, Cambridge, Mass.). The plate was incubated at room temperature for thirty minutes, then rinsed three times with distilled water. One hundred microliters of 1% polyvinyl alcohol (w/v) in PBS was added to each well, and the plate was incubated at room temperature for sixty minutes, after which it was rinsed as above.

A Standard Reference Material (SRM) 3128 (National Institute of Standards and Technology, Gaithersburg, Md.) consisting of 10 mg/ml lead nitrate in 10% $HNO_3$ was diluted-tenfold in 1.0 M HEPES, pH 9.5. This solution was diluted to a final concentration of 100 µg/ml in 0.1 M HEPES, pH 8.0. One hundred microliters of the resulting solution was added to each well of the plates treated with the EKY polymer. The plates were incubated for 30 minutes and washed three times with distilled water before being used for ELISA.

One hundred microliters of hybridoma culture fluid to be assayed for the presence of lead cation monoclonal antibodies was added to the well of an antigen-coated microtiter plate. The assay plate was incubated for 30 minutes at room temperature. The plate was then rinsed three times with ELISA wash (0.1% Triton X 100 in PBS) and three times with distilled water. One hundred microliters of a 1:1000 dilution of goat anti-mouse IgA, IgG, IgM (Kirkegaard and Perry Laboratories, Gaithersburg, Md.) conjugated to horseradish peroxidase was added to each well. The plate was incubated at room temperature for thirty minutes, then rinsed as described above. After one hundred microliters of ABTS peroxidase substrate (Kirkegaard and Perry Laboratories) were added to each well and the plate was incubated at room temperature for fifteen minutes. The absorbance of each well at 405 nanometers was then measured on a Bio Tek Model EL-311 Plate Reader (Fisher, Pittsburgh, Pa.). The measured absorbances were compared to the absorbance of an average of four control wells. A hybridoma was considered positive if the absorbance of an assay well containing lead was twice that of a control well to which no lead had been added.

Positive hybridomas were subcloned by limiting dilution in 96-well microtiter plates in medium consisting of 50% HT medium and 50% complete DMEM conditioned by buffalo rat liver cells. Buffalo rat liver cells are known to secrete several somatomedin growth factors into the medium during growth. The somatomedin growth factors enhance the growth of cells in cloning situations.

3. Precipitation of Monoclonal Antibodies from Ascites Fluid

Ascites fluid was centrifuged at 300g for 10 minutes at 4° C. to remove any particulate matter. The supernant fluid was decanted into a centrifuge tube and chilled in an ice bath for fifteen minutes. An ammonium sulfate solution was prepared by mixing 9 parts of a saturated solution of ammonium sulfate with 1 part distilled water. The resulting ammonium sulfate solution was added dropwise to an equal volume of ascites fluid while stirring gently. The mixture was stirred for an addition 4 hours at 4° C. The precipitate was pelleted by centrifugation at 3000 g for 30 minutes at 4° C. The pellet was resuspended in and dialyzed against PBS at 4° C.

The volume of the dialysate was measured, and two volumes of 60 millimolar sodium acetate, pH 4.0, was added to bring the final pH to 4.8. Caprylic acid (Sigma Chemical Co.) was added dropwise at a ratio of 0.4 milliliters per ten milliliters of the original volume of 20 ascites fluid. The mixture was stirred at 4° C. for four hours and centrifuged as above. The pellet was resuspended in PBS and dialyzed against PBS with 0.05% Triton X-100 for 24 hours then against PBS for 24 hours.

4. Measurement of the Sensitivity of the Lead-Specific Monoclonal Antibodies by ELISA ELISA was carried out essentially as described in subsection 2 above except that the lead nitrate solution was diluted to final concentrations of 100, 50, 10, 5, or 1 µg/ml using 0.1 M HEPES, pH 8.0. One hundred microliters of each of these solutions was then added to the plate coated with the polyamino acid mixture. Caprylic acid-precipitated mAb was adjusted to a concentration of 50 µg/ml, and 100 µl was added to the appropriate wells of the microliter plate. The plate was incubated for 30 minutes at room temperature, and the ELISA was continued as described above.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

| SEQUENCE ID NO. DESIGNATIONS | | |
| --- | --- | --- |
| SEQ ID NO: | ANTIBODY NAME | DESCRIPTION |
| 1 | 6B11 | heavy chain |
| 2 | 1254 | heavy chain |
| 3 | 8E7 | heavy chain |
| 4 | 10G5 | heavy chain |
| 5 | 14F11 | heavy chain |
| 6 | 6B11 | heavy chain |
| 7 | 1254 | heavy chain |
| 8 | 14F11 | heavy chain |
| 9 | 13D10 | heavy chain |
| 10 | 11D11 | heavy chain |
| 11 | 14G11 | light chain |
| 12 | 6F5 | light chain |
| 13 | 7D10 | light chain |
| 14 | 4E8 | light chain |
| 15 | 10G5 | light chain |
| 16 | 2E7 | light chain |
| 17 | 7D10 | heavy chain |
| 18 | 2B4 | heavy chain |
| 19 | 2E7 | heavy chain |
| 20 | | n.a. primer |
| 21 | | n.a. primer |
| 22 | | n.a. primer |
| 23 | | n.a. primer |
| 24 | | n.a. primer |
| 25 | | n.a. primer |

We claim:

1. A lead binding polypeptide comprising a light chain variable region from a monoclonal antibody capable of binding a lead cation, wherein the light chain variable region includes carboxylic acid side chain group-containing amino acid residues in at least two of positions 30, 32 and 92, and wherein the lead binding polypeptide does not include a heavy chain variable region.

2. The lead binding polypeptide of claim 1 wherein the light chain variable region includes asparatic acid residues in positions 30, 32 and 92.

3. The lead binding polypeptide of claim 1 comprising a fusion protein which includes the light chain variable region.

4. The lead binding polypeptide of claim 1 wherein the light chain variable region is from a $V_k32$ light chain.

5. The polypeptide of claim 1 comprising a $F_{ab}$ fragment light chain which includes the light chain variable region.

6. The polypeptide of claim 1 wherein the light chain variable region has a variable region amino acid sequence from monoclonal antibody 6B11 (SEQ ID NO:12).

7. The polypeptide of claim 1 wherein the light chain variable region has a variable region amino acid sequence from monoclonal antibody 1254 (SEQ ID NO:14).

8. The polypeptide of claim 1 wherein the light chain variable region has a variable region amino acid sequence from monoclonal antibody 14F11 (SEQ ID NO:15).

9. The polypeptide of claim 1 wherein the light chain variable region has a variable region amino acid sequence from monoclonal antibody 10G5 (SEQ ID NO:29).

10. The polypeptide of claim 1 wherein the light chain variable region has a variable region amino acid sequence from monoclonal antibody 7D10 (SEQ ID NO:34).

11. The lead binding polypeptide of claim 1, wherein the light chain variable region includes aspartic acid residues in positions 28, 30, 31, 32 and 92.

12. A kit comprising a lead binding polypeptide including a light chain variable region from a monoclonal antibody capable of binding a lead cation, wherein the light chain variable region includes carboxylic acid side chain group-containing amino acid residues in at least two of positions 30, 32 and 92, and wherein the lead binding polypeptide does not include a heavy chain variable region and a buffer.

13. The kit of claim 6 wherein the lead binding polypeptide comprises a $F_{ab}$ fragment light chain which includes the light chain variable region.

14. An isolated nucleotide sequence comprising a first sequence encoding a light chain variable region from a monoclonal antibody capable of binding a lead cation, wherein the light chain variable region includes carboxylic acid side chain group-containing amino acid residues in at least two of positions 30, 32 and 92, and wherein the lead binding polypeptide does not include a heavy chain variable region.

15. The isolated nucleotide sequence of claim 14 wherein the isolated nucleotide sequence codes for a polypeptide capable of binding a lead cation.

16. The isolated nucleotide sequence of claim 15 wherein the polypeptide comprises a $F_{ab}$ fragment light chain which includes the light chain variable region.

17. The isolated nucleotide sequence of claim 14 wherein the first sequence encodes a light chain variable region from monoclonal antibody 6B11 (SEQ ID NO:11), monoclonal antibody 1254 (SEQ ID NO:13), monoclonal antibody 14F11 (SEQ ID NO:15), monoclonal antibody 10G5 (SEQ ID NO:29), or monoclonal antibody 7D10 (SEQ ID NO:33).

18. The isolated nucleotide sequence of claim 14 wherein the light chain variable region includes aspartic acid residues in positions 30, 32 and 92.

19. The isolated nucleotide sequence of claim 14, wherein the light chain variable region includes aspartic acid residues in positions 28, 30, 31, 32 and 92.

* * * * *